US010758673B2

United States Patent
Hyde et al.

(10) Patent No.: US 10,758,673 B2
(45) Date of Patent: Sep. 1, 2020

(54) SYSTEMS FOR DISPENSING A MEDICAMENT TO A SUBJECT AND RELATED METHODS

(71) Applicant: Elwha LLC, Bellevue, WA (US)

(72) Inventors: Roderick A. Hyde, Redmond, WA (US); Muriel Y. Ishikawa, Livermore, CA (US); Jordin T. Kare, San Jose, CA (US); Max N. Mankin, Seattle, WA (US); Nathan P. Myhrvold, Bellevue, WA (US); Tony S. Pan, Bellevue, WA (US); Robert C. Petroski, Seattle, WA (US); Elizabeth A. Sweeney, Seattle, WA (US); Clarence T. Tegreene, Mercer Island, WA (US); Nicholas W. Touran, Seattle, WA (US); Yaroslav A. Urzhumov, Bellevue, WA (US); Lowell L. Wood, Jr., Bellevue, WA (US); Victoria Y. H. Wood, Livermore, CA (US)

(73) Assignee: ELWHA LLC, Bellevue, WA (US)

( * ) Notice: Subject to any disclaimer, the term of this patent is extended or adjusted under 35 U.S.C. 154(b) by 273 days.

(21) Appl. No.: 15/068,461

(22) Filed: Mar. 11, 2016

(65) Prior Publication Data
US 2017/0258995 A1    Sep. 14, 2017

(51) Int. Cl.
| | | |
|---|---|---|
| *A61M 5/172* | (2006.01) | |
| *A61B 5/11* | (2006.01) | |
| *A61B 5/00* | (2006.01) | |
| *A61B 7/00* | (2006.01) | |
| *A61M 35/00* | (2006.01) | |

(Continued)

(52) U.S. Cl.
CPC ............. *A61M 5/1723* (2013.01); *A61B 5/00* (2013.01); *A61B 5/11* (2013.01); *A61B 5/4839* (2013.01); *A61B 7/00* (2013.01); *A61H 1/006* (2013.01); *A61M 35/00* (2013.01); *A61M 37/00* (2013.01); *A61B 5/6805* (2013.01); *A61F 13/00* (2013.01); *A61M 5/14* (2013.01); *A61M 37/0015* (2013.01); *A61M 2205/18* (2013.01); *A61M 2205/3303* (2013.01)

(58) Field of Classification Search
CPC ........................... A61M 5/1723; A61M 37/00
USPC ..................................................... 604/890.1
See application file for complete search history.

(56) References Cited

U.S. PATENT DOCUMENTS

| | | |
|---|---|---|
| 6,962,600 B2 | 11/2005 | Lennox et al. |
| 2001/0027282 A1 | 10/2001 | Baugh |

(Continued)

FOREIGN PATENT DOCUMENTS

| | | | | |
|---|---|---|---|---|
| WO | WO 2010007565 A2 * | 1/2010 | ........... | A61K 9/0009 |
| WO | WO 2016/009277 A1 | 1/2016 | | |

OTHER PUBLICATIONS

Al-Mulla et al. "An Autonomous Wearable System for Predicting and Detecting Localised Muscle Fatigue" Sensors 2011, 11, 1542-1557.

(Continued)

*Primary Examiner* — Phillip A Gray
(74) *Attorney, Agent, or Firm* — Dorsey & Whitney LLP

(57) ABSTRACT

Embodiments disclosed herein are directed to systems and methods of dispensing one or more medicaments to a subject. The systems and methods utilize at least one flexible compression garment having one or more medicament dispensers therein.

51 Claims, 11 Drawing Sheets

(51) Int. Cl.
  *A61H 1/00*   (2006.01)
  *A61M 37/00*  (2006.01)
  *A61F 13/00*  (2006.01)
  *A61M 5/14*   (2006.01)

(56) References Cited

U.S. PATENT DOCUMENTS

| | | |
|---|---|---|
| 2004/0081680 A1 | 4/2004 | Pesce et al. |
| 2006/0030915 A1 | 2/2006 | Lennox et al. |
| 2007/0087901 A1 | 4/2007 | Brassil et al. |
| 2010/0105998 A1* | 4/2010 | Benni ............... A61B 5/6846 |
| | | 600/340 |
| 2010/0286600 A1* | 11/2010 | Bommannan ........ A61K 9/0021 |
| | | 604/66 |
| 2012/0109047 A1 | 5/2012 | Yodfat et al. |
| 2014/0148741 A1* | 5/2014 | Moran ............... A41D 13/0015 |
| | | 601/84 |
| 2015/0124566 A1* | 5/2015 | Lake ................... G04G 21/08 |
| | | 368/10 |

OTHER PUBLICATIONS

European Patent Office, Extended European Search Report, Pursuant to Rule 62 EPC; App. No. EP 17763920.0; dated Oct. 29, 2019 (received by our Agent on Oct. 25, 2019); pp. 1-10.

* cited by examiner

SYSTEMS FOR DISPENSING A MEDICAMENT TO A SUBJECT AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Compression garments including clothing articles (e.g., socks, arm sleeves, leg sleeves, joint sleeves, etc.) can conform to and provide support to muscles of a body part on which the compression garments are worn. This support can be useful for people who have to stand for long periods, or people with circulation problems.

Compression sportswear, which is a specific type of compression garment, can also be worn during exercise. For example, bicycling shorts are a common type of compression sportswear. Compression sportswear can improve muscle functioning, and prevent chafing and rashes during and after exercise.

Compression garments can have a number of positive effects on a user. For example, compression garments can help relieve pain from muscle stiffness and soreness, and reduce time taken for muscles to repair themselves. Also, when an appropriate amount of compression is used, compression garments can improve venous return and oxygenation to working muscles.

Despite the availability of a number of different compression garments, manufacturers and users of compression garments continue to seek improvements thereto.

SUMMARY

Embodiments disclosed herein are directed to systems for and methods of dispensing one or more medicaments to a subject wearing at least one flexible compression garment. In an embodiment, a system for dispensing one or more medicaments to a subject is disclosed. The system includes at least one flexible compression garment. The system further includes at least one medicament dispenser disposed on or in the at least one flexible compression garment and one or more actuators configured to selectively deliver the one or more medicaments. The at least one medicament dispenser includes the one or more medicaments therein. The system includes a controller operably coupled to the one or more actuators. The controller is configured to direct the one or more actuators to manage delivery of the medicament from the at least one medicament dispenser.

In an embodiment, a method of dispensing one or more medicaments to a subject is disclosed. The method includes at least one flexible compression garment contacting at least one body part of the subject. The at least one flexible compression garment includes at least one medicament dispenser disposed on or in the at least one flexible compression garment, the at least one medicament dispenser including the one or more medicaments therein and one or more actuators. The method further includes, via a controller operably coupled to the one or more actuators, directing the one or more actuators to selectively manage delivery of the one or more medicaments in the at least one medicament dispenser to the subject responsive to one or more signals.

In an embodiment, a method of dispensing one or more medicaments to a subject is disclosed. The method includes with at least one flexible compression garment, contacting at least one body part of the subject. The at least one flexible compression garment includes at least one medicament dispenser disposed on or in the at least one flexible compression garment. The at least one medicament dispenser includes the one or more medicaments therein and one or more actuators. The method further includes at the one or more actuators, receiving one or more signals that direct the one or more actuators to selectively delivery the one or more medicaments in the at least one medicament dispenser to the subject.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
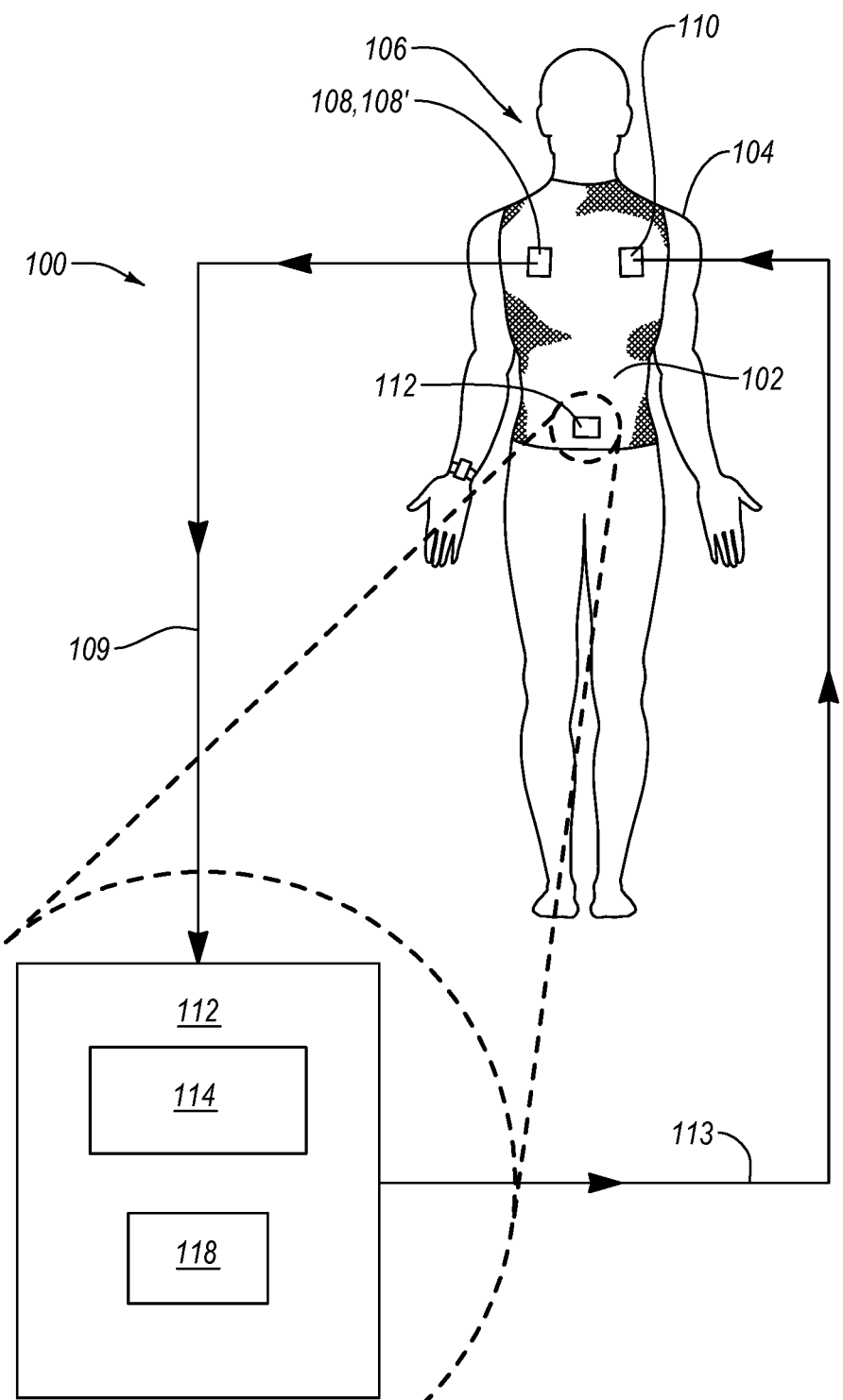
FIG. 1A is a schematic view of a system for dispensing medicaments, according to an embodiment.

Embodiments disclosed herein relate to systems for selectively dispensing one or more medicaments to a subject wearing at least one flexible compression garment. The systems include at least one flexible compression garment, at least one medicament dispenser having one or more actuators disposed on or in the at least one flexible compression garment, and a controller operably coupled to the at least one medicament dispenser. In one or more embodiments, the systems include one or more sensors and one or more actuators that operate responsive to one or more signals from the one or more sensors to selectively deliver one or more medicaments. Such selective delivery can provide timely relief from certain physical symptoms, improve performance, stop or alleviate potentially dangerous medical conditions, or improve muscle or joint functioning during a sport or other activity of the subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

FIG. 1A is a schematic view of a system 100 for dispensing medicaments, according to an embodiment. The system 100 includes a flexible compression garment 102 that is configured to be worn on at least one body part 104 of a subject 106 during use. The system 100 further includes one or more medicament dispensers 110 positioned relative to (e.g., in or on) the flexible compression garment 102 and configured to selectively deliver the one or more medicaments therein. The one or more medicament dispensers 110 include one or more actuators (FIGS. 3A-3D) therein. The system 100 further includes a controller 112 operably coupled to the one or more medicament dispensers 110, such as being operably coupled to and configured to selectively direct the one or more actuators to manage delivery of the one or more medicaments from the one or more medicament dispensers 110.

The medicament delivery systems disclosed herein can include one or more medicaments composed to treat one or more maladies, provide comfort to a wearer, enhance performance, alleviate fatigue, alleviate activity-related symptoms (e.g., over-heating, soreness, swelling, etc.), prevent injury, or prevent emergencies (e.g., alleviate breathing problems, cardiac problems, or pulmonary problems). The one or more medicaments disclosed herein can include one or more of an anesthetic, an analgesic, an anti-inflammatory (e.g., a non-steroidal anti-inflammatory drug such as aspirin, ibuprofen, naproxen, or a COX-2 inhibitor), a rubefacient, a warming agent, a coagulant (e.g., styptic), an anti-coagulant, a cooling agent, a salicylate, a vasodilator, a vasoconstrictor, an antiseptic, a hormone, a steroid, a corticosteroid, a vitamin, a nutrient, a mineral, or any other medicament composed to treat a physical condition. For example, in an embodiment, the cooling agent can include one more ketals, carboxamides, cyclohexyl derivatives (e.g., menthols including one or more isomers thereof), or any other suitable cooling agent. In an embodiment, the one or more medicaments can be dispensed as a fluid (e.g., a liquid, cream, lotion, ointment, gas, foam, etc.). The fluid can be a mixture of one or more medicaments, such as in a solution, a dispersion, an emulsion, a suspension, a gel, or any of mixture of the foregoing substances. In an embodiment, the one or more medicaments can be dispensed as a solid (e.g., a dissolvable solid in an emulsion or bound to the surface of a protrusion).

In the illustrated embodiment, the system 100 includes one or more sensors 108 operably coupled to the controller 112 and supported by the at least one flexible compression garment 102. As discussed in more detail below, the one or more sensors 108 or 108' can be configured to sense one or more of physiological data (e.g., body temperature, strain or stress on a body part, chemical composition of body fluid(s), etc.), environmental data (e.g., ambient temperature, distance traveled, etc.), or other data (e.g., duration of an activity) associated with the subject 106. Responsive to sensed data 109 from the one or more sensors 108, the controller 112 is configured to (i.e., includes at least one of software, circuitry or a processor programmed to) direct the one or more actuators to selectively manage delivery of the one or more medicaments, via one or more signals 113. However, as discussed in more detail below, in other embodiments, the one or more sensors 108 or 108' can be omitted.

The controller 112 is configured to receive the sensed data 109 (via wired or wireless connections) from the one or more sensors 108 or 108', determine (e.g., with a processor therein) if a medicament is required or requested, and send one or more signals 113 to the one or more medicament dispensers 110 (e.g., one or more actuators in the medicament dispenser(s)) to direct actuation thereof. Sending the one or more signals 113 can be responsive to the sensed data 109.

Figure 1B:
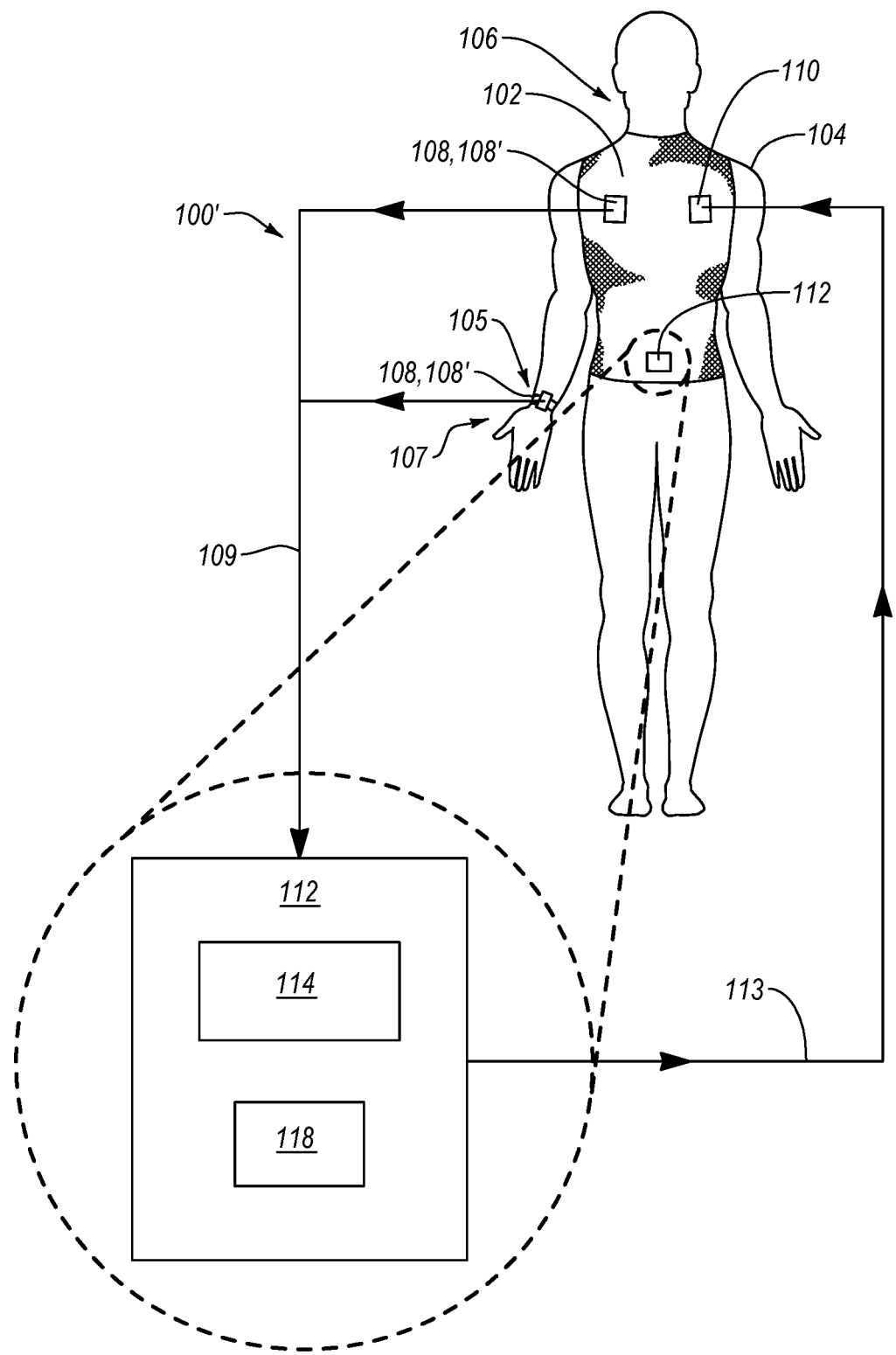
FIG. 1B is a schematic view of a system for dispensing medicaments, according to an embodiment.

In an embodiment, the one or more sensors can be positioned separately from the at least one compression garment 102. FIG. 1B is a schematic view of a system 100' for dispensing medicaments, according to an embodiment.

The system 100' includes a flexible compression garment 102 that is configured to be worn on at least one body part 104 of a subject 106 during use. The system 100' includes one or more medicament dispensers 110 positioned relative to (e.g., in or on) the flexible compression garment 102 and configured to selectively deliver or control delivery of the one or more medicaments therein. The one or more medicament dispensers include one or more actuators therein. The system 100' includes a controller 112 operably coupled to the one or more medicament dispensers 110, such as being operably coupled to and configured to selectively direct the one or more actuators to manage delivery of the one or more medicaments from the one or more medicament dispensers 110. The system 100' can include one or more sensors 108 or 108' operably coupled to the controller 112 and supported by the at least one flexible compression garment 102 or one or more wearable devices 107. The one or more wearable devices 107 can include one or more of another flexible compression garment (e.g., a joint, leg, or arm sleeve), a band (e.g., a wrist, arm, leg, or head band), a brace (e.g., knee, wrist, ankle, neck, or elbow brace), a watch (e.g., wristwatch), a hat, a patch, a bandage, a wrap, an article of clothing, a necklace, a belt, a strap, a glove, a ring, footwear (e.g., shoes, sandals, or socks), an ear bud, jewelry, etc. In an embodiment, the wearable device 107 can be attached to the body part 105 by an attachment device (e.g., adhesive, hook and loop material, clips, or other suitable device). For example, the wearable device 107 can be configured as a patch, bandage, epidermal electronics, or the like, having an attachment device configured to connect to the subject 106. The wearable device 107 can support one or more sensors 108 or 108' therein or thereon. The wearable device 107 can be worn remotely (e.g., on a different region or body part of the subject) from the at least one flexible compression garment 102. Responsive to sensed data 109 from the one or more sensors 108 or 108', the controller 112 can direct the one or more actuators of the one or more medicament dispensers 110 to selectively manage delivery of the one or more medicaments, via one or more signals 113.

The controller 112 is configured to receive sensed data 109 (via wired or wireless connections) from the one or more sensors 108 or 108', determine if a medicament is required or requested, and send one or more signals 113 to the one or more medicament dispensers 110 (e.g., one or more actuators in the medicament dispenser(s)) to direct actuation thereof, which can be responsive to the sensed data 109.

The flexible compression garment 102 can be substantially tubular and configured to generally conform to the at least one body part when worn thereon. The flexible compression garment 102 can be made from any suitable material. For example, the flexible compression garment 102 can be made from neoprene, nylon, synthetic rubber, cotton, wool, or any other suitable synthetic or natural fabric or polymeric material. The at least one flexible compression garment 102 can be configured to conform to at last one body part of a wearer such as one or more of a leg including the upper leg (e.g., thigh or quadriceps), the lower leg (e.g., calf), or knee joint therebetween; an ankle; a foot; a toe; an arm including an upper arm, forearm, or an elbow joint therebetween; a wrist; a hand; a finger; a neck; a head; a hip; a torso (e.g., chest, back, waist, or abdomen); gluteus maximus; or at least a portion of any of the foregoing. The at least one flexible compression garment 102 can be configured to provide contact between the one or more sensors or one or more medicament dispensers 110 disposed therein or thereon and the soft tissue of the wearer, such as at any of the above listed body parts.

Figure 2A:
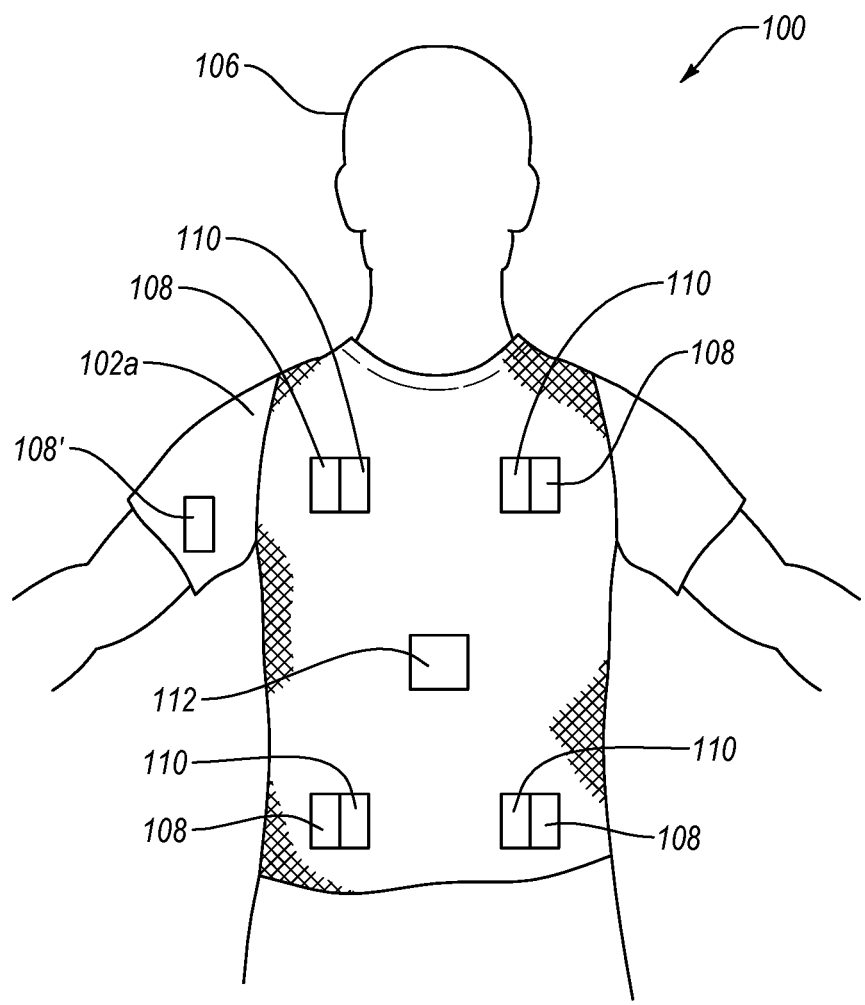
FIG. 2A is a schematic view of a system for dispensing medicaments configured as a flexible compression garment, according to an embodiment.

In an embodiment, the flexible compression garment 102 can be configured as clothing, such as athletic clothing, casual clothing, support clothing, etc. FIG. 2A is an embodiment of a flexible compression garment 102a configured as a shirt. The flexible compression garment 102a can include one or more sensors 108 or 108' associated therewith. The one or more sensors 108 or 108' can be disposed in different regions of the flexible compression garment 102a. For example, a plurality of sensors 108 can be disposed in the flexible compression garment 102a about the torso of the subject 106 while another sensor 108' can be disposed on a sleeve of the flexible compression garment 102a. The one or sensors 108 or 108' can be mounted on, embedded in, or otherwise supported by the flexible compression garment 102a. As discussed in more detail below, the sensors 108 and 108' can be configured to sense the same data or different data respectively.

The flexible compression garment 102a includes one or more medicament dispensers 110 thereon. The one or more medicament dispensers 110 can be disposed adjacent to or remote from the one or more sensors 108 or 108'. For example, each of the one or more sensors 108 can be disposed adjacent to (e.g., in contact with) one or more corresponding medicament dispensers 110. The flexible compression garment 102a can include the controller 112 thereon. For example, the controller 112 can be mounted on, embedded in, or otherwise supported by the flexible compression garment 102a. In an embodiment, each of the medicament dispensers 110 can be controlled by the controller 112 responsive to sensed data from the adjacent one of the one or more sensors 108. The sensed data can be communicated to the controller 112. The controller 112 (e.g., a processor therein) can be configured to determine if the one or more medicaments need to be released, increased, decreased, maintained, or stopped from the one or more medicament dispensers 110. In an embodiment, one or more of the medicament dispensers 110 can be controlled by the controller 112 responsive to sensed data from the any of the one or more sensors 108 or 108'. In an embodiment, each of the medicament dispensers 110 can be controlled by the controller 112 responsive only to sensed data from the adjacent one of the one or more sensors 108 or the sensor 108'.

Figure 2B:
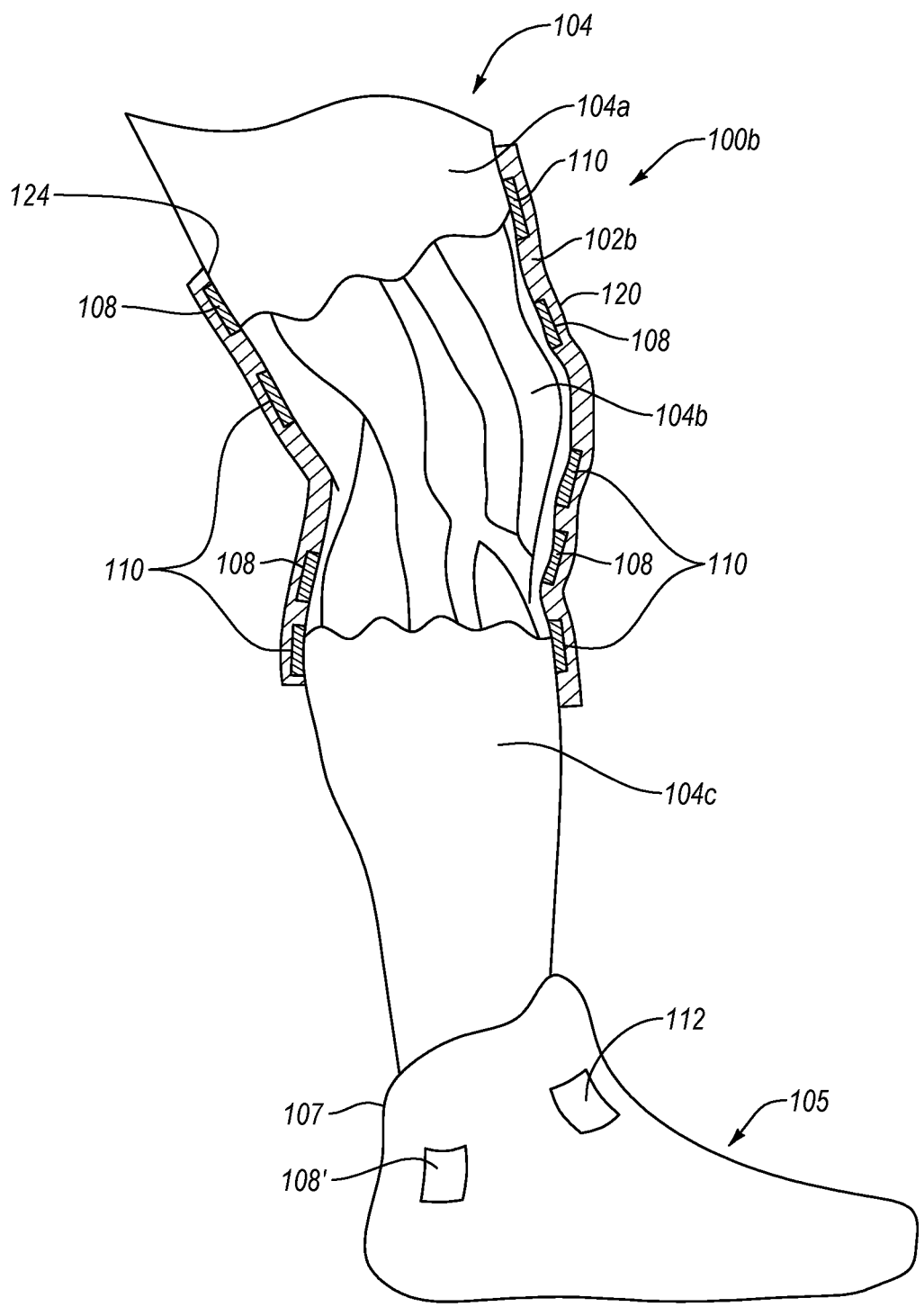
FIG. 2B is a schematic view of a system for dispensing medicaments including a flexible compression garment, according to an embodiment.

In an embodiment, the flexible compression garment can be substantially tubular and configured to conform to (e.g., maintain contact with) a body part of a subject. FIG. 2B is an embodiment of a system 100b including a flexible compression garment 102b configured as a leg sleeve. The at least one body part 104 is a leg of the user, which can include one or more of a portion of the subject's upper leg 104a, such as a thigh, lower leg 104c such as a calf, or knee joint 104b therebetween, that is received by the flexible compression garment 102b. However, the systems disclosed herein can be employed on any other body part(s). For example, the at least one body part 104 of the subject 106 can include one or more of at least a portion of an upper arm, forearm, an elbow joint therebetween, a wrist, a hand, a foot, a neck, a head, a hip, a torso, or at least a portion of any of the foregoing. Thus, in an embodiment, the flexible compression garment 102 can be configured as a limb sleeve (e.g., arm sleeve or leg sleeve), a joint sleeve (e.g., elbow, knee, ankle, wrist, or finger sleeve), a shirt, an undershirt, a girdle, an abdominal support, a back support, gloves, shorts, pants, socks, a brace, or other article of clothing.

The flexible compression garment 102b can include one or more sensors 108 disposed therein. The one or more sensors 108 can be disposed at or adjacent to an interior surface 124 of the flexible compression garment 102b, such as to come in direct contact with the subject. In such embodiments, the one or more sensors 108 can sense physiological, environmental, or other data. Physiological data can be sensed directly (e.g., via direct contact) from the subject and can include temperature of a body part, stress in a body part, strain on a body part, chemicals present in a body fluid located at a body part, etc.

In an embodiment, one or more sensors can be located remotely from the flexible compression garment 102b. For example, a wearable device 107 having one or more sensors 108' can be disposed on another body part 105 of the subject. The one or more sensors 108' can be configured to sense physiological, environment, or other data associated with the subject at another location on the subject than at the least one flexible compression garment 102b. In an embodiment, the sensor 108' can be configured to sense the same, similar, or different data than the one or more sensors 108. For example, in an embodiment, the one or more sensors 108 can be configured to sense a temperature or chemical composition of a body fluid in a specific location on a subject while the sensor 108' can be configured to sense a number of steps a subject has taken or an ambient temperature of an environment the subject is currently in.

In an embodiment, the wearable device 107 is configured to be worn on an additional (e.g., separate or distinct) body part 105 than the at least one body part 104 on which the at least one flexible compression garment 102 is configured to be worn. Thus, the wearable device 107 is separate and distinct from the at least one flexible compression garment 102. For example, the wearable device 107 can be configured as footwear and the flexible compression garment 102 can be configured as an arm sleeve. In an embodiment, the wearable device 107 is configured to be worn on an additional, adjacent but separate body part than the at least one body part 104 on which the at least one flexible compression garment 102 is configured to be worn. For example, as shown in FIG. 2B, the wearable device 107 can be configured as footwear and the flexible compression garment 102 can be configured as a leg sleeve that is worn on the same or different leg as the footwear. In an embodiment, the wearable device 107 is configured to be worn on the at least one body part 104 that the at least one flexible compression garment 102 is configured to be worn on, but remain separate and distinct from the flexible compression garment 102. For example, the wearable device 107 can be configured as footwear such as a shoe and the flexible compression garment 102 can be configured as a sock. In an embodiment, the wearable device 107 can include any of the flexible compression garments disclosed herein, and can be worn on any of the corresponding body parts disclosed herein, where the wearable device 107 and the flexible compression garment 102 are separate articles. In an embodiment, the wearable device 107 can be a band (e.g., a wrist or headband), an article of jewelry, a watch, a ring, footwear, an article of clothing, a flexible compression garment, a patch, a wrap, etc.

In an embodiment, the controller 112 can be located on or in the wearable device 107 or another additional wearable device (not shown). The controller 112 can be mounted on, embedded in, or otherwise supported by the wearable device 107, such as in or on footwear as shown. The controller 112 is configured to receive the sensed data from the one or more sensors 108 or 108' and determine if medicament delivery needs to be initiated, maintained, increased, decreased, or stopped. Responsive to the determination, the controller 112 can be configured to send a signal to the one or more medicament dispensers 110 (or actuators therein) to direct the one or more medicament dispensers 110 to manage delivery of the one or more medicaments therein. For example, responsive to a sensed swelling in a body part of the subject, controller 112 can determine that an anti-inflammatory medicament needs to be administered, and responsive thereto, send a corresponding signal to the medicament dispenser 110 effective to cause delivery of the anti-inflammatory medicament.

Figure 2C:
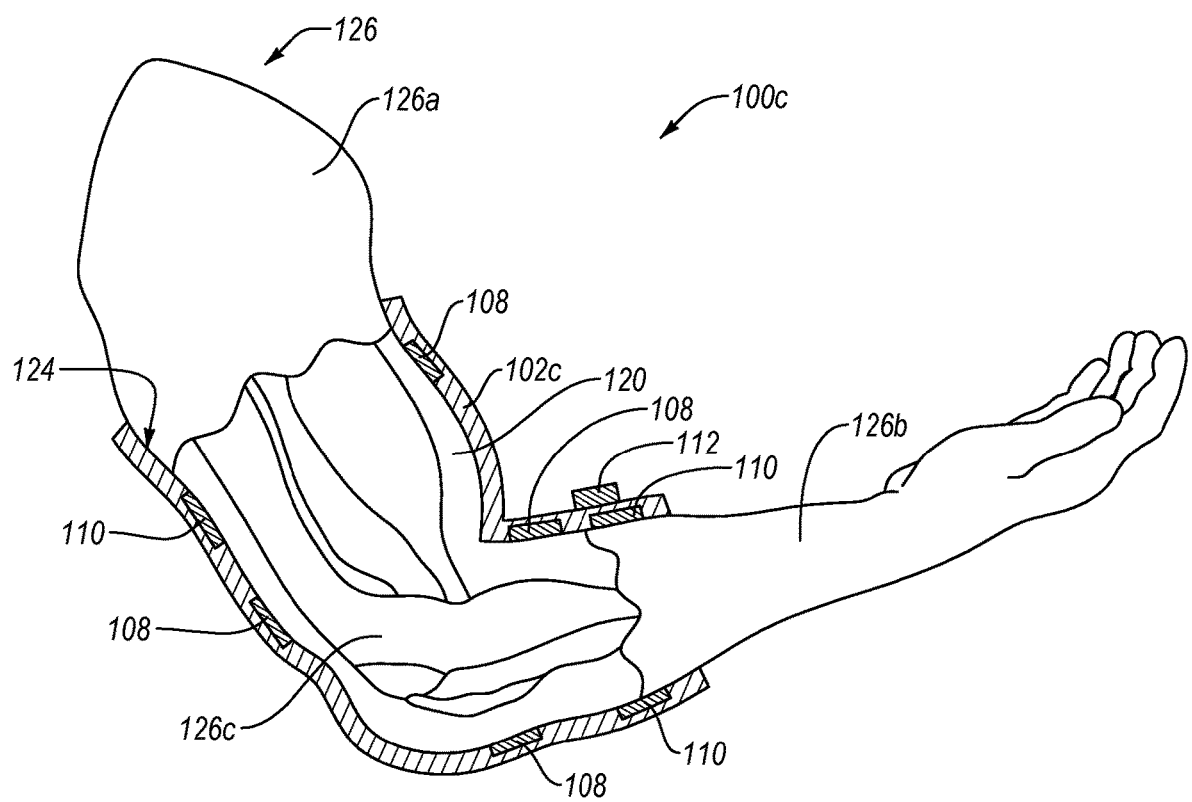
FIG. 2C is a schematic view of a system for dispensing medicaments including a flexible compression garment, according to an embodiment.

FIG. 2C is an embodiment of a system 100c including a flexible compression garment 102c configured as an arm sleeve. The at least one body part 126 is an arm of the subject, which can include one or more of a portion of the subject's 106 upper arm 126a such as a bicep, lower arm 126b such as a forearm, or an elbow joint 126c therebetween that is received by the flexible compression garment 102b. The flexible compression garment 102c can include one or more sensors 108 disposed therein. The one or more sensors 108 can be disposed at or adjacent to an interior surface 124 of the flexible compression garment 102c, such as to come in direct contact with the subject.

In an embodiment, each of the sensors 108 can be configured to sense the same, similar, or different data than the one or more sensors 108. For example, in an embodiment, the one or more sensors 108 can be configured to sense a chemical composition of a body fluid at a specific location on a subject while another sensor 108 can be configured to detect pressure or sound indicating a pulse of the subject in a specific location.

In an embodiment, a plurality of medicament dispensers 110 can be mounted on, embedded in, or otherwise supported by the at least one flexible compression garment 102c, such as in the arm sleeve as shown. For example, the plurality of medicament dispensers 110 can be disposed on the interior surface 124 of the flexible compression garment 102c as shown. In such embodiments, at least some of the plurality of medicament dispensers 110 can be at least partially in contact with the subject (e.g., in contact with the skin or other soft tissue of a subject). In an embodiment, at least a portion of one or more of the plurality of medicament dispensers 110 can be disposed in the flexible compression garment 102c such as at least partially encapsulated therein. In such an embodiment, the medicament dispensers 110 can be configured to deliver one or more medicaments through at least a portion of the at least one compression garment, such as via pores, needles, or micro-protrusions extending therethrough. In an embodiment, the inner surface of the flexible compression garment is configured to cause one or more of the sensors to be in contact with the skin of the subject 106.

In an embodiment, the controller 112 can be mounted on, embedded in, or otherwise supported by the at least one compression garment 102c, such as on the arm sleeve as shown in FIG. 2C. In an embodiment, the controller 112 can be embedded at least partially in the compression garment 102c. In such an embodiment, the controller 112 can be protected from the elements, such as cold, heat, fluids (e.g., water, sweat, blood, etc.), or from impacts. The controller 112 is configured to receive the sensed data from the one or more sensors 108 and determine if medicament delivery needs to be initiated, maintained, increased, decreased, or stopped. Responsive to the determination, the controller 112 can be configured to send a signal to direct the one or more medicament dispensers 110 (or actuators therein) to manage delivery of the one or more medicaments therein.

Figure 2D:
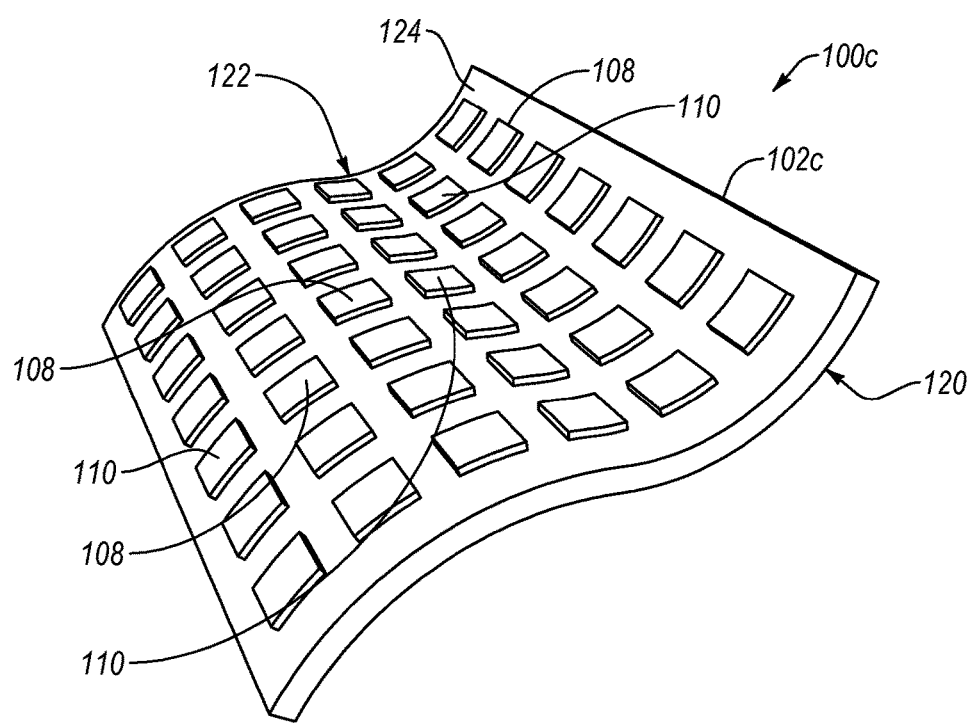
FIG. 2D is an isometric view of a portion of the flexible compression garment of FIG. 2C.

FIG. 2D is an isometric view of an interior surface of the flexible compression garment 102*c* of the system 100*c* shown in FIG. 2C. The flexible compression garment 102*c* includes an exterior surface 120 and an interior surface 124. In an embodiment, the flexible compression garment 102*c* can be formed as a substantially or at least partially tubular body wherein the interior surface 124 defines an interior space 122. In an embodiment, one or more medicament dispensers 110, one or more sensors 108, the controller 112, or portions of one or more thereof can be disposed about the interior surface 124 of the flexible compression garment 102*c*. For example, the one or more sensors 108 and one or more medicament dispensers 110 can be disposed circumferentially about and along the interior surface 124 of the flexible compression garment 102*c*. For example and as shown, one or more sensors 108 and one or more medicament dispensers 110 can be disposed in the interior surface 124 of the flexible compression garment 102*c* and can be in direct contact with the subject. The interior surface 124 can be configured to isolate the one or more sensors 108 or one or more medicament dispensers 110 from external contact, such as contact with the skin of the subject 106. In an embodiment, the one or more medicament dispensers 110, one or more sensors 108, or controller 112 can be embedded internally within the flexible compression garment 102*c*. In an embodiment, the flexible compression garment 102*c* can include one or more medicament dispensers 110, one or more sensors 108, the controller 112, or portions of one or more thereof can be disposed about the exterior surface 120 of the at least one flexible compression garment 102*c*. For example and as shown, the controller 112 can be positioned on the exterior surface 120 of the flexible compression garment 102*c*.

The one or more medicament dispensers 110, the one or more sensors 108, or the controller 112 can be disposed on any portion of the flexible compression garment. For example, the one or more sensors 108 can be located in the flexible compression garment at a position therein configured to correspond to an anatomical feature of the subject (e.g., at a joint, at a point suitable for determining a pulse or blood pressure, at sweat gland, etc.) when worn by the subject. In an embodiment, the one or more medicament dispensers 110 can be disposed in the flexible compression garment in a location configured to correspond to a specific body part or specific place on a body part. For example, the one or more medicament dispenser 110 can be positioned on the flexible compression garment in a location corresponding to a portion of the dermis know to absorb a topically applied medicament, or adjacent to a muscle for which the medicament is composed to treat (e.g., close to a quadriceps of a subject when the medicament is a liniment). In an embodiment, the controller 112 can be disposed in the flexible compression garment in a location configured to be accessed (e.g., seen or manipulated) by the subject or a location configured to experience the fewest impacts, during use. For example, the one or more medicament dispenser 110 can be positioned on the flexible compression garment in a location corresponding to the inside of the lower arm of the subject as shown in FIG. 2D.

As mentioned above, the one or more sensors 108 can be configured to sense one or more of physiological data (e.g., body temperature, electrical property of a tissue or body fluid, optical property of a tissue or body fluid, strain or stress on a body part, chemical composition of body fluid(s), etc.), environmental data (e.g., ambient temperature, distance traveled, etc.), or other data (e.g., duration of an activity or time since the medicament was last dispensed) associated with the subject 106. For example, the sensed data can be at least one physiological characteristic, at least one chemical characteristic (e.g., biochemical or biological), or at least one spatial or temporal characteristic (e.g., distance traveled, force exerted, duration of exertion, etc.) associated with the subject 106 or a body part thereof. The sensed data can include sensed information regarding one or more of nerve activity of a body part of the subject, presence or temperature of one or more body fluids of the subject, one or more chemicals in a body fluid of the subject, temperature in a body part of the subject, heart rate of the subject, pulse in a body part of the subject, oxygenation of a body part of the subject, acoustic emission from at least one joint or muscle of the subject, or swelling in a body part of the subject. The sensed data can include sensed information regarding one or more of a change in motion of travel of the subject, a load applied to the one or more sensors by a body part of the subject, pressure applied to the one or more sensors by a body part of the subject, tension applied to the one or more sensors by a body part of the subject, torque applied to the one or more sensors by a body part of the subject, velocity of at least a body part of the subject, acceleration of at least a body part of the subject, location of the subject, gait of the subject, or pace at which the subject moves. The sensed data can include information regarding one or more of a load on a body part of the subject, pressure on a body part of the subject, tension on a body part of the subject, location of the subject, distance that the subject has traveled, duration of the exertion by the subject or a body of the subject, time, or temperature of an ambient environment of the subject.

In an embodiment, the one or more sensors 108 are configured to only sense the at least one characteristic of at least one muscle of the subject 106, while in other embodiments, the one or more sensors 108 are configured to only sense at least one characteristic of at least one joint of the subject 106. In an embodiment, a plurality of the one or more sensors can be disposed in a cluster in a region of the at least one flexible compression garment, with each of the one or more sensors being configured to sense a different data type (e.g., a first sensor measures temperature, a second sensor measures a pulse, a third sensor measures chemical composition of a body fluid, and a fourth sensor measures nerve activity). In an embodiment, a plurality of the one or more sensors can be disposed in different regions of the subject (such as on at least one flexible compression garment or wearable device), with each of the one or more sensors being configured to sense the same or different one or more characteristics (e.g., data types).

In any of the embodiments disclosed herein, the one or more sensors 108 can include at least one of an electromyographic sensor, a mechanomyographic sensor, kinematic sensor, a thermal sensor (e.g., temperature sensor), a muscle oxygenation sensor, an acoustic sensor, an accelerometer, a pedometer, a counter, a tension sensor (e.g., tension meter), a pressure sensor (e.g., pressure gauge), a strain gauge, a timer (e.g., watch, stop-watch, etc.), a pulse sensor, heart rate sensor, a kinetic sensor, an oximeter, a global positioning system (GPS) receiver, an altimeter, a resistance meter, a voltage meter (e.g., multimeter), a chemical sensor, a biochemical sensor, an optical sensor, an acoustic sensor, or a biosensor.

In an embodiment, the one or more sensors 108 are configured to sense onset of or a threshold level of at least one of activity, temperature, chemical content, stress, strain, blood oxygenation, exertion or any other characteristic disclosed herein. In such an embodiment, the controller 112 (a processor therein) is configured to determine if the onset of a requirement for delivery of a medicament or a threshold level has been reached or exceeded and direct the one or more medicament dispensers 110 (e.g., actuators therein) to selectively deliver or manage delivery of the one or more medicaments responsive thereto. In an embodiment, the controller 112 can direct the one or more medicament dispensers 110 (or actuators therein) to selectively deliver or control delivery of the one or more medicaments according to an operational program associated with sensed data, sensed data type, or threshold level.

One suitable sensor configured to sense nerve impulses of at least one muscle (e.g., indicative of the onset of the muscle activity or a change in muscle activity) includes one or more electrical sensors such as electromyography sensors and apparatus, which can be attached, adhered, or embedded within the at least one flexible compression garment 102 or wearable device 107, or can be attached directly to the subject 106. For example, responsive to sensing the onset of muscle fatigue via the one or more electromyography sensors, the controller 112 can direct the one or more medicament dispensers 110 (e.g., actuator(s) therein) to selectively deliver or control delivery of the one or more medicaments responsive thereto. The electromyography sensors can detect electrical signals indicative of the strength of muscle contractions or other signs of fatigue. Examples of suitable electromyography sensors and equipment can include surface electromyography sensors (e.g., bipolar electrodes or a piezoelectric thin film sensor) or inserted electromyography sensors (e.g., needle electrodes).

In an embodiment, one or more sensors 108 can be electrical sensors configured to detect one or more electrical properties of a soft tissue (e.g., the skin) or a body fluid of the subject. Responsive to said electrical properties or changes therein, the controller 112 can direct the one or more medicament dispensers to selectively manage delivery of the one or more medicaments therein.

In an embodiment, the one or more sensors 108 are configured to sense an injury of the subject 106. For example, the one or more sensors 108 can be configured to detect a level or change in one or more of a pace of the subject 106, gait of the subject 106, pulse of the subject 106, load on a body part, tension on a body part, pressure on a body part, or strain on a body part inconsistent with an established level for that specific characteristic. As another example, the one or more sensors 108 can be configured to detect a limp in the subject 106, or that the subject 106 is favoring a foot, a leg, or an arm, such as by comparing current sensed data with baseline or model sensed data for the same at least one characteristic. As yet another example, the one or more sensors 108 can be configured to detect an oxygen content, lactic acid content, hydration level, or other body fluid characteristic associated with an injury or cause of impaired performance. In another example, the one or more sensors 108 can be configured to detect swelling in a body part of the subject, such as by pressure exerted by the swelling or displacement of one or more sensors due to the swelling.

In an embodiment, the one or more sensors 108 can be one or more optical sensors (e.g., laser doppler imaging) configured to detect one or more characteristics or properties of a soft tissue or body fluid of the subject (e.g., oxygenation of a muscle).

In an embodiment, the one or more sensors 108 can include one or more passive infrared thermal sensors. For example, each passive infrared thermal sensor is positioned on or in the at least one flexible compression garment 102 or wearable device 107 and is configured to sense infrared radiation from the subject 106 or a body part of the subject 106. An increase in the infrared radiation can be indicative of or correlated with increased muscle temperature, which can be indicative of increased muscle activity. A decrease in the infrared radiation can be indicative of or correlated with decreased muscle temperature, which can be indicative of decreased muscle activity. For example, responsive to sensing an increase in or a threshold level of infrared radiation, the controller 112 can direct the one or more medicament dispensers 110 to selectively deliver or control delivery of the one or more medicaments. As another example, responsive to sensing a decrease in or an amount less than a threshold level of infrared radiation, the controller can direct the one or more medicament dispensers 110 to selectively deliver or control delivery of the one or more medicaments due to detected muscle activity decreasing.

In an embodiment, the one or more sensors 108 can be at least one thermal sensor configured to sense the temperature of the ambient environment of the subject, temperature of the subject, or the temperature of a body part of the subject either directly or indirectly.

In an embodiment, the one more sensors 108 can include one or more muscle oxygenation sensors or an oximeter. For example, each muscle oxygenation sensor can include a near infrared sensor positioned and configured to deliver light in the near infrared spectrum to at least one muscle of the subject 106 and detect light reflected from the at least one muscle (e.g., tissue), thereby sensing absorption of the near infrared light by the muscle that differs in oxygenated and deoxygenated tissues. Changes in the absorption of near infrared light from the at least one muscle can be correlated with or can be indicative of increased or decreased muscle oxygenation. For example, changes in the absorption of the near infrared light can be associated with increased exertion or decreased muscle oxygenation (e.g., associated with overwork, cramping, claudication, or other impaired performance).

In an embodiment, responsive to sensing a change in muscle oxygenation, the controller 112 can direct the one or more medicament dispensers 110 to selectively deliver or control delivery of the one or more medicaments. For example, responsive to sensing an increase in muscle oxygenation over a threshold level, the controller 112 can direct the one or more medicament dispensers 110 to selectively deliver or control delivery of the one or more medicaments due to detected muscle oxygenation increasing. For example, responsive to sensing a decrease in muscle oxygenation below a threshold level, the controller 112 can direct the one or more actuators (FIGS. 3A-3D) to cause the one or more medicament dispensers 110 to selectively deliver or control delivery of the one or more medicaments due to detected muscle oxygenation decreasing.

In an embodiment, the one or more sensors 108 can include multiple near infrared source-detector pairs that can measure spatial and regional differences in skeletal muscle oxygenation or localized changes in the subject 106. For example, responsive to sensing a localized decrease in infrared radiation below a threshold level indicative of significantly decreased muscle oxygenation and blood flow associated with a muscle cramp, the controller 112 can direct the one or more medicament dispensers 110 to selectively deliver or control delivery of the one or more medicaments. For example, responsive to sensing a varied decrease in infrared radiation indicative of a gradient of decreased muscle oxygenation and blood flow associated with muscle overexertion, the controller can direct the one or more actuators to cause the one or more medicament dispensers 110 to selectively deliver or control delivery of the one or more medicaments to only a part of the at least one body part 104 to provide localized treatment of the body part 104. In other embodiments, the one or more near infrared sensors can be used to sense a change in joint inflammation.

In an embodiment, the one more sensors 108 can include one or more acoustic transducers configured to irradiate the one or more body parts with acoustic radiation and receive reflected acoustic radiation responsive thereto. The received reflected acoustic radiation can be correlated with or can be indicative of muscle activity or joint activity of one or more body parts including the at least one body part 104. For example, a relatively stronger/more intense reflected acoustic radiation received by the one or more acoustic transducers can be indicative of relatively tenser, more active muscles, while a relatively weaker/less intense reflected acoustic radiation received by the one or more acoustic transducers can be indicative of relatively looser, less active muscles.

In an embodiment, the acoustic transducer includes an ultrasound transducer, and each of the acoustic radiation and the reflected acoustic radiation includes ultrasound radiation. The received reflected ultrasound radiation can be correlated with or can be indicative of at least one characteristic of one or more body parts including the at least one body part 104. For example, altered echogenicity detected by the one or more acoustic transducers can be indicative of swelling or inflammation of the muscle. For example, altered echogenicity detected by the one or more acoustic transducers can be indicative of joint effusion of the at least one joint. For example, Doppler ultrasound sensing of the at least one muscle can detect increased blood flow within the at least one muscle, indicating increased activity of the at least one muscle. For example, Doppler ultrasound sensing of a ligament or tendon can detect limited activity within the ligament or tendon, indicating stress to the region. In an embodiment, responsive to the one or more acoustic transducers detecting a change acoustic characteristics of at least one body part, the controller can be configured to direct the one or more medicament dispensers 110 to selectively deliver or control delivery of the one or more medicaments at or near the location of the body part exhibiting at least one change of acoustic characteristic. For example, responsive to sensing echogenicity indicating an increase in muscle or joint activity, the controller 112 can direct the one or more medicament dispensers 110 to selectively deliver or control delivery of the one or more medicaments. For example, responsive to sensing echogenicity indicating a decrease in muscle or joint activity, the controller can direct the one or more medicament dispensers 110 to selectively deliver or control delivery of the one or more medicaments due to a determination of muscle activity decreasing based upon acoustic data. For example, responsive to sensing echogenicity indicating inflammation in the least one muscle or the at least one joint, controller can direct the one or more medicament dispensers 110 to selectively deliver or control delivery of the one or more medicaments.

In an embodiment, the one more sensors 108 can include one or more acoustic myography sensors positioned and configured to sense acoustic emission from a body part, such as the at least one body part 104. For example, responsive to sensing a high frequency by the acoustic myography sensor, indicative of increased muscle use, the controller can direct the one or more medicament dispensers 110 to selectively deliver or control delivery of the one or more medicaments around at least one muscle of the at least one body part 104.

In an embodiment, the one more sensors 108 can include one or more acoustic sensors positioned and configured to sense acoustic emission from at least one joint. For example, the one or more acoustic sensors can be positioned adjacent to or proximate to at least one joint (e.g., an ankle, a wrist, or a knee) so that the one or more acoustic sensors can receive acoustic emission from the at least one joint that can be indicative of joint problems, such as aggravation of an arthritic or an osteoarthritic condition and resultant arthralgia. For example, responsive to sensing acoustic emission or an increase in acoustic emission from the at least one joint, the controller can direct the one or more the one or more medicament dispensers 110 to selectively deliver or control delivery of the one or more medicaments near or at the at least one joint and the at least one muscle around the at least one joint of the at least one body part 104 to thereby alleviate arthralgia.

In an embodiment, the one more sensors 108 can include one or more of at least one chemical sensor, at least one biochemical sensor, or at least one biosensor configured to detect an analyte from a body fluid, a dermal tissue, a muscle, or a joint of the of the subject 106. For example, at least one chemical sensor, at least one biochemical sensor, or at least one biosensor can be configured to detect at least one of an ion, a salt, glucose, a lactate, lactic acid, an anti-body, a cytokine, or an inflammatory marker molecule. Body fluids can include any of one or more of blood, sweat, saliva, mucus, or interstitial fluids of the subject. In an embodiment, the one or more sensors can include a chemical sensor configured to determine the amount of chloride, lactic acid, urea, cortisol, or water in sweat or saliva. For example, responsive to sensing an increase in lactic acid in at least one muscle indicative of muscle fatigue using a biosensor, the controller 112 can direct the one or more the one or more medicament dispensers 110 to selectively deliver or control delivery of the one or more medicaments at or near the at least one muscle of the subject 106. In an embodiment, a chemical sensor can detect the level (e.g., threshold level) of salt in sweat from a subject. For example, the amount of salt in the sweat of a subject 106 indicates possible hypernatremia (e.g., dehydration) or hyponatremia and the symptoms thereof, including imminent cramping. Responsive to sensing an undesirable salt level in the sweat of a subject 106 being indicative of hypernatremia, the controller 112 can direct the one or more the one or more medicament dispensers 110 to selectively deliver or control delivery of the one or more medicaments around at least one body part 104 of the subject 106. In an embodiment, one or more biochemical sensors can be positioned and configured to detect the amount of glutamate, prostaglandin, bradykinin, serotonin, adenosine triphosphate, lactate, pyruvate, salts or components thereof, any other compounds in a body fluid, or combinations of any of the foregoing in the body fluid of the subject, such as in an interstitial fluid.

In an embodiment, the at least one chemical sensor, at least one biochemical sensor, or at least one biosensor can be configured to sense the amount of or effect of the one or more medicaments in a body fluid of the subject at any point before, during, or after dispensing. In such an embodiment, the one or more sensors can be used to provide a feedback loop to the system to determine the efficacy of the one or more medicaments. Responsive thereto, the controller can be configured to actively monitor and adjust the amount of medicament dispensed to the subject via the one or more medicament dispensers. Any of the sensors herein can be used to provide a feedback loop to the system based on one or more of physiological, environment, or other characteristics of the subject. Such feedback can be used to actively monitor and control the amount of medicament(s) dispensed to the subject.

In an embodiment, the one more sensors 108 can include one or more accelerometers positioned and configured to sense acceleration, deceleration, trends thereof, or patterns thereof, of a subject 106 or body part of the subject 106, such as the at least one body part 104 or at least an additional body part 105. For example, responsive to sensing deceleration in an activity rate by the accelerometer, the controller 112 can direct the one or more the one or more medicament dispensers 110 to selectively deliver or control delivery of the one or more medicaments. In another example, responsive to sensing acceleration in an activity rate by the accelerometer, the controller 112 can direct the one or more the one or more medicament dispensers 110 to selectively deliver or control delivery of the one or more medicaments.

In an embodiment, the one more sensors 108 can include at least one of one or more kinematic sensors such as counters (e.g., a pedometer) positioned and configured to count a specific incidence of physical activity or movement of the subject 106 or body part of the subject 106 (e.g., footsteps, pedal rotation cycle, arm movement, tackles in football, laps, etc.), such as the at least one body part 104 or at least an additional body part 105. For example, responsive to sensing a specific number of footfalls or strides with a pedometer, the controller 112 can direct the one or more the one or more medicament dispensers 110 to selectively deliver or control delivery of the one or more medicaments. In another example, responsive to sensing a specific number of footfalls on a pedometer, the controller 112 can direct the one or more the one or more medicament dispensers 110 to selectively deliver or control delivery of the one or more medicaments. In an embodiment, responsive to a specific number of counts, such as arm swings as measured by a kinematic sensor, the controller 112 can direct the one or more the one or more medicament dispensers 110 to selectively deliver or control delivery of the one or more medicaments. In an embodiment, the one more kinematic sensors can include a goniometer, e.g., to measure the angle of a joint. For example a goniometer can be used in conjunction with an electromygraphic sensor or mechanomyographic sensor and/or with an acoustic sensor (e.g., ultrasound) to measure localized muscle fatigue.

In an embodiment, the one more sensors 108 can include one or more tension sensors (e.g., a strain gauge, a force transducer, or a universal-force moment sensor) configured to detect or measure tension on a body part of the subject 106, such as one or more muscles, tendons, or ligaments. For example, responsive to receiving sensed data of tension beyond a threshold level on at least one body part 104 or at least an additional body part 105 of a subject 106, the controller 112 can direct the one or more the one or more medicament dispensers 110 to selectively deliver or control delivery of the one or more medicaments, such as at or near the area where the threshold levels was sensed. For example, responsive to determining that a threshold level of strain has taken place on a ligament or muscle, the controller 112 can direct the one or more medicament dispensers 110 adjacent to the ligament or muscle to dispense a liniment. In an embodiment, the controller 112 can also direct the one or more medicament dispensers 110 near other ligaments or muscles to selectively deliver the liniment to those ligaments or muscles. In an embodiment, responsive to receiving sensed data of tension below a threshold level on a body part of a subject 106, the controller 112 can direct the one or more the one or more medicament dispensers 110 to selectively deliver or control delivery of the one or more medicaments. In an embodiment, responsive to the one or more sensors 108 detecting a tension of a body part, the controller 112 can direct the one or more the one or more medicament dispensers 110 to selectively deliver or control delivery of the one or more medicaments according to a preprogrammed routine (e.g., time release, multiple dosage releases, increasing amounts, decreasing amounts, etc.).

In an embodiment, the one more sensors 108 can include one or more pressure sensors (e.g., a piezoelectric sensor or strain gauge, a force or pressure transducer, a capacitive pressure sensor, or an electromagnetic pressure sensor) configured to detect pressure, load, or force exerted by or through a body part of the subject 106 on the one or more sensors 108 or force on a body part of the subject 106 (e.g., at a foot, joint, or muscle). For example, responsive to receiving sensed data of pressure or force beyond a threshold level on the at least one body part 104 or at least an additional body part 105 of a subject 106, the controller 112 can direct the one or more medicament dispensers 110 to selectively deliver or control delivery of the one or more medicaments, such as around an ankle or leg. In an embodiment, strain and pressure sensors can be used over time to sense pressure or tension in the at least one body part 104 or at least an additional body part 105 as a function of time. Both strain and pressure sensors can also be used to determine if swelling or inflammation is present or measure the extent of the swelling in a body part of the subject 106 and adjust the delivery or control of the one or more medicaments, as desired. For example, responsive to receiving sensed data of pressure or force above a threshold, indicative of swelling of the body part 104, the controller 112 can direct the one or more medicament dispensers 110 to selectively deliver or control delivery of the one or more medicaments. As an example, responsive to sensing indication of swelling, the controller 112 can direct the one or more the one or more medicament dispensers 110 to selectively deliver or control delivery of an anti-inflammatory.

For example, responsive to receiving sensed data of pressure or force below a threshold level on a body part of a subject 106, the controller 112 can direct the one or more the one or more medicament dispensers 110 to selectively deliver or control delivery of the one or more medicaments to the body part(s) of the subject. In an embodiment, responsive to the one or more sensors 108 detecting pressure or force on a body part, or force exerted on one or more sensors 108 by a body part of the subject 106, the controller 112 can direct the one or more the one or more medicament dispensers 110 to selectively deliver or control delivery of the one or more medicaments according to a preprogrammed routine (e.g., time release, multiple dosage releases, increasing amounts, decreasing amounts, etc.).

In an embodiment, the one more sensors 108 can include one or more time-keepers configured to detect the duration of an activity or duration of use or exertion of a body part, such as the at least one body part 104 or at least an additional body part 105. For example, responsive to passage of a specific duration of time or time of day, the controller 112 can direct the one or more medicament dispensers 110 to selectively deliver or control delivery of the one or more medicaments. In an embodiment, responsive to the passage of a specific duration of time or a time of day, the controller 112 can direct the one or more medicament dispensers 110 to selectively deliver or control delivery of the one or more medicaments according to a preprogrammed routine.

In an embodiment, the one more sensors 108 can include a global positioning system (GPS) receiver or an altimeter configured to detect a distance traveled, velocity of the subject 106 or a body part of the subject 106, or an elevation of the subject 106. For example, responsive to sensing a specific distance traveled or elevation at which the selected activity is taking place, the controller 112 can direct the one or more the one or more medicament dispensers 110 to selectively deliver or control delivery of the one or more medicaments. As an example, responsive to sensing a specific distance traveled or elevation at which the selected activity is taking place, the controller 112 can direct the one or more the one or more medicament dispensers 110 to selectively deliver or control delivery of a vasodilator. In an embodiment, responsive to detecting a specific distance traveled or elevation at which the specific activity is taking place, the controller 112 can direct the one or more the one or more medicament dispensers 110 to selectively deliver or control delivery of the one or more medicaments according to a preprogrammed routine.

In an embodiment, the one more sensors 108 can include one or more pulse sensors configured to measure a pulse in a body part of the subject 106 (e.g., a peripheral pulse in an artery in a foot, ankle, wrist, or other body part). Thus, in an embodiment, the one or more pulse sensors can be selectively positioned on the flexible compression garment 102 or the wearable device 107 to be proximate to an artery of the subject 106. For example, a pulse sensor can include an optical pulse sensor, such as those used in fitness bracelets, or an acoustic sensor. In an embodiment, responsive to sensing an increase in the peripheral pulse rate or a pulse rate above a threshold pulse rate in the at least one body part 104 or at least an additional body part 105 of the subject 106 (indicative of increased muscle activity within the body part), the controller 112 can direct the one or more medicament dispensers 110 to selectively deliver or control delivery of the one or more medicaments such as to the at least one body part 104. As another example, responsive to sensing a decrease in the pulse rate in the at least one body part 104 or at least an additional body part 105 of the subject 106 (indicative of decreased muscle activity within the body part 104 or 105), the controller 112 can direct the one or more the one or more medicament dispensers 110 to selectively deliver or control delivery of the one or more medicaments.

In an embodiment, one more optional additional types of sensors 108' can be incorporated into flexible compression garment 102 or wearable device 107 (e.g., footwear in FIG. 2B) and operably coupled to the controller 112. In an embodiment, the one or more additional types of sensors can include one or more heart rate sensors that are configured to sense a heart rate of the subject 106 or one or more electrocardiography sensor. For example, the sensor 108' can include a sensor that is incorporated into the flexible compression garment 102 or wearable device 107 configured as a chest band and worn around a torso. The sensor 108' can be configured to sense heart rate or electrocardiographic activity of the subject 106. For example, the one or more sensors 108' can include a flexible low profile sensor that is embedded in a material of the wearable device 107 and in direct or indirect contact with the torso, and is configured to sense heart rate or electrocardiographic activity of the subject. In an embodiment, the one or more heart rate sensors can include a pulse sensor for measuring a peripheral pulse, such as in a limb, as described above.

Responsive to sensing an increase in the heart rate of the subject 106 indicative of increased overall muscle activity, the controller 112 can direct the one or more the one or more medicament dispensers 110 to selectively deliver or control delivery of the one or more medicaments. As another example, responsive to sensing a decrease in the heart rate of the subject 106 indicative of decreased muscle activity, the controller 112 can direct the one or more the one or more medicament dispensers 110 to selectively deliver or control delivery of the one or more medicaments.

By way of another example and having applicability to any of the sensors 108 or optional additional types of sensors 108' disclosed herein, in an embodiment, directing the one or more medicament dispensers 110 to deliver or control delivery of one or more medicaments is responsive to the controller (e.g., processor therein) determining that at least one characteristic sensed by the one or more sensors is indicative of the subject 106 or a body part of the subject 106 being injured or being strained past a strain limit. In another embodiment having applicability to any of the sensors 108 disclosed herein, directing the one or more medicament dispensers 110 to deliver or control delivery of one or more medicaments is responsive to the controller (e.g., processor therein) determining that at least one characteristic sensed by the one or more sensors 108 being indicative of the at least one muscle being exerted, such as beyond a threshold level. In another embodiment having applicability to any of the one or more sensors 108 disclosed herein, directing the one or more medicament dispensers 110 to deliver or control delivery of one or more medicaments is responsive to the controller 112 (e.g., processor therein) determining that at least one characteristic sensed by the one or more sensors 108 being indicative of at least one muscle not being exerted beyond a threshold level. For example, the sensed data (e.g., sensed physiological characteristics) from the one or more sensors 108 can indicate that at least one muscle is not being exerted at or near a physiological or functional limit thereof, and the controller 112 can be configured to adjust the directions to the medicament dispensers 110 to stop, decrease, maintain, start, or increase the amount of medicament dispensed around the at least one muscle based thereon.

In an embodiment, one or more of any of the different types of sensors 108, 108' described herein can be used in the same system 100, such as being disposed in the same flexible compression garment 102, multiple flexible compression garments 102, the same wearable device 107, multiple wearable devices 107, or combinations thereof used simultaneously on the same or different body parts of the subject 106. For example, at least one pressure sensor and at least one accelerometer can be disposed in each of the flexible compression garments 102 such as leg sleeves worn on both legs of a subject 106. During a time period or an activity, such as running, sensed data from the pressure sensors and the accelerometers in each leg sleeve can be compared by the controller 112 to determine forces involved in the activity, a level of activity, a type of activity, an indication of a limp or other injury to the subject 106, duration of the activity, or any other detectable characteristics. A reduced pressure applied by or to one foot or change in accelerometer data for one limb of the subject 106 can indicate that the subject 106 is favoring a specific leg and therefore likely injured. Responsive to detection of a limp in one the limbs of the subject 106, the controller 112 can direct the one or more medicament dispensers 110 to selectively deliver or control delivery of the one or more medicaments around the limb based on the controller 112 determining that the sensed data is indicative of a limp. Likewise, any of the other types of sensors herein can be used to sense data indicating differences in characteristics (e.g., chemical content or make-up of a body fluid) in different body parts or regions of a body part of the subject 106. In such embodiments, the controller 112 (e.g., a processor therein) can be configured to determine if the difference requires (e.g., is indicative of a treatable injury or physical condition) selective dispensing of a medicament, and can be configured to direct the one or more actuators to control delivery of the one or more medicaments based on the determination.

A combination of the any of the different types of the one or more sensors 108, 108' disclosed herein can be used to determine one or more physiological conditions of the subject 106 (e.g., pulse, oxygenation, general health, etc.), the level of exertion of the subject in an activity, injury to the subject, or any characteristic associated with the subject (e.g., time, ambient environment temperature, etc.) as described herein. Such a determination can be carried out by the controller 112, such as by a processor therein as described in detail below.

Returning to FIG. 2D, in an embodiment, a corresponding medicament dispenser 110 can be positioned adjacent to a specific one or set of the one or more sensors 108. In an embodiment, the one or more sensors 108 can detect one or more sensed data indicative of a condition at or near the position of the sensors 108. In such an embodiment, the medicament dispenser 110 and controller 112 can be configured to cause the medicament to be delivered responsive only to the sensed data from the adjacent one or more sensors 108. In an embodiment, the controller 112 and medicament dispenser(s) 110 can be configured to cause delivery of the one or more medicaments responsive to sensed data from some or all of the one or more sensors 108.

In an embodiment, at least some of the medicament dispensers 110 can include a different medicament than other medicament dispensers 110 in the system. In such an embodiment, a first medicament dispenser(s) 110 and the controller 112 can be configured to cause the first medicament dispenser(s) 110 (or the actuators therein) to manage or direct (e.g., initiate, increase, maintain, decrease, or stop) the delivery the first medicament therein responsive to one or more first signals based on the first sensor data type (e.g., only based on body temperature or a detected fluid type or content). For example, the controller 112 can be configured to determine if an alteration or maintenance of the delivery of the first medicament is necessary based on specific sensed data from the sensor(s) 108 adjacent to the first medicament dispenser(s) 110. Such specific sensed data can include one or more of any of the types of sensed data herein, such as temperature, heart rate, pulse in a body part, chemical make-up of body fluid(s), blood or tissue oxygenation, duration of activity, etc. In such embodiments, a second medicament dispenser(s) 110 and the controller 112 can be configured to cause the second medicament dispenser(s) 110 (or the actuators therein) to manage the delivery a second medicament therein responsive to one or more second signals based on the second sensor data type different from the first sensor data type. For example, the controller 112 can be configured to determine if an alteration or maintenance of the delivery of the second medicament is necessary based on specific sensed data from the sensor(s) 108 adjacent to the second medicament dispenser(s) 110, when the second sensed data type is different from the first sensed data type. Systems herein can include one or more different medicaments stored in one or more different medicament dispensers 110, such as 2 or more medicaments, 3 or more, or 4 or more medicaments stored in corresponding medicament dispensers 110.

In an embodiment, more than one medicament can be stored and dispensed from the same medicament dispenser 110 (e.g., a single dispenser having multiple reservoirs and actuators corresponding thereto). In such an embodiment, the controller 112 (e.g., a processor therein) can be configured to determine if the sensed data indicates that a change or maintenance in the delivery state of at least some of the one or more the medicaments is required. Responsive thereto, the controller 112 can provide a corresponding signal to the actuator(s) in the one or more medicament dispensers 110 to direct the selective delivery of one or more selected medicaments (e.g., corresponding to a condition related to the sensed data) therein.

The one or more medicament dispensers 110 disclosed herein can be configured to provide one or more of topical, transdermal, intradermal, subcutaneous, intramuscular, or oral delivery of the one or more medicaments to the soft tissue (e.g., skin, muscle, etc.) of a subject 106. Suitable medicament dispensers 110 can include iontophoretic delivery systems, one or more needles, micro-protrusion arrays (e.g., medicament coated micro or nano-needles arrays), medicament containing patches, medicament containing reservoirs in fluid communication with one or more output apertures (e.g., pores, needle(s), etc.), plungers, constriction devices, or other delivery means. The one or more medicament dispensers 110 disclosed herein can have many configurations, such as any of those described below. For example, a medicament dispenser can include one or more reservoirs having one or more medicaments therein and one or more actuators configured to selectively move the one or more medicaments from the one or more reservoirs to an output aperture or surface, such as a pore, micro-protrusion, needle, patch, etc.

The one or more medicament dispensers 110 disclosed herein can include one or more actuators configured to manage (e.g., effect or cause the initiation, increase, maintenance, decrease, or cessation of) delivery of the one or more medicaments in the one or more medicament dispensers 110. In an embodiment, the one or more actuators of the one or more medicament dispensers can include one or more plungers or constriction devices configured to reduce in interior space of the at least one reservoir effective to cause at least some the one or more medicaments therein to be dispensed therefrom. Further examples of actuators can include a fluid displacement actuator including one or more piezoelectric actuators, one or more springs, one or more solenoids, one or more valves, one or more magnets, one or more motors (e.g., electrical motors or micro-motors), one or more compressed gas actuators, one or more gear systems, one or more electrodes, or one or more energy source.

Figure 3A:
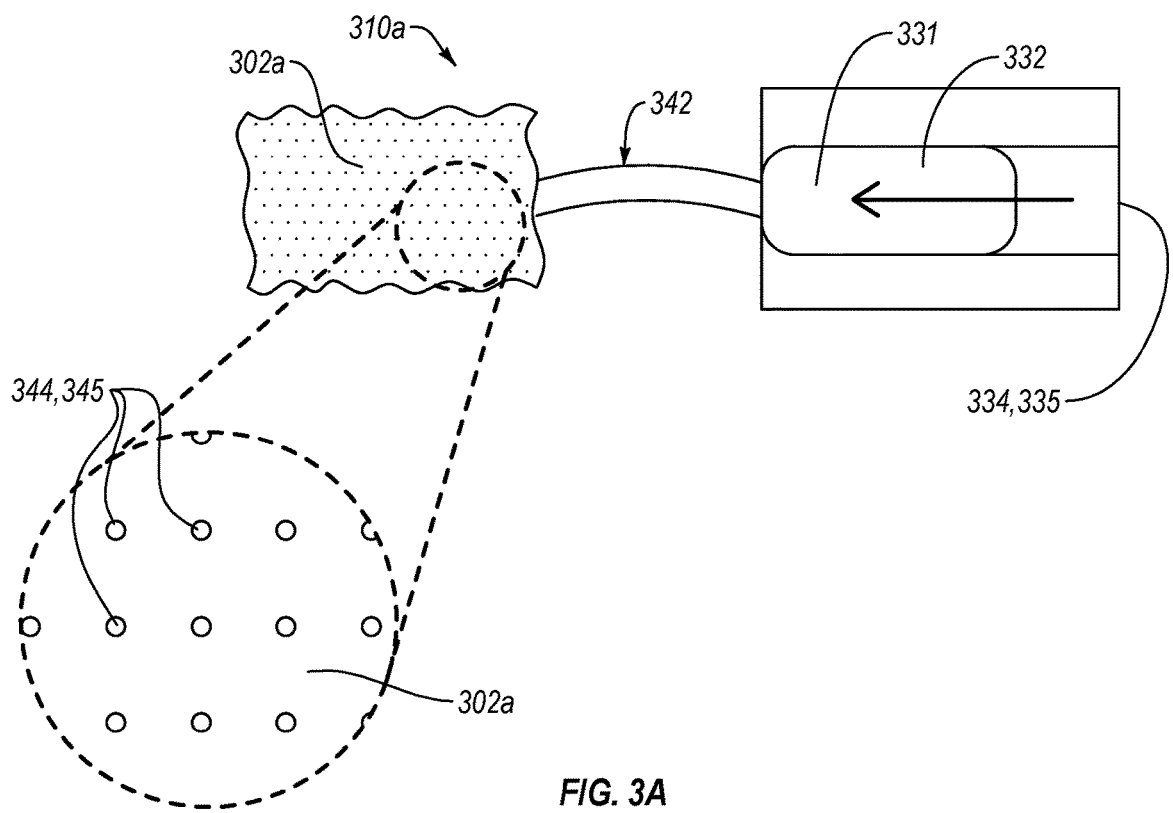
FIG. 3A is a schematic view of a medicament dispenser, according to an embodiment.

FIG. 3A is a schematic view of a medicament dispenser 310a according to an embodiment. The medicament dispenser 310a can include one or more reservoirs 332, one or more medicaments 331 disposed in the one or more reservoirs 332, at least one actuator 334 configured to selectively manage (e.g., cause the initiation, increase, maintenance, decrease or stop of) the delivery of the one or more medicaments 331 responsive to one or more signals from the controller 112 (not shown), one or more output apertures 340, and one or more conduits 342 between the one or more reservoirs and the one or more output apertures 344.

In an embodiment, the one or more reservoirs 332 can have a configuration suitable to hold nanoliter (nl) quantities (e.g., about 1 or more nl, such as about 1-500 nl, about 1-100 nl, about 1-50 nl, about 1-30 nl, about 1-15 nl, or less than 500 nl), microliter (µl) quantities (e.g., 1 or more µl, such as 1-500 µl, 1-100 µl, 250-750 µl, or 500 to 1000 µl), or milliliter (ml) quantities (e.g., 1 or more ml, such as 1-500 ml, 1-10 ml, or 1-3 ml) of the one or more medicaments. The one or more reservoirs 332 can include at least one actuator 334 operably coupled thereto and configured to cause or control the selectively delivery of the one or more medicaments from the one or more reservoirs 332. In an embodiment, each of the one or more reservoirs can be fluidly coupled to a second reservoir configured to replenish the one or more medicaments in the one or more reservoirs after actuation of the medicament dispensers. In an embodiment, the one or more reservoirs can include a bag, a tube (e.g., a syringe), a chamber, a porous medicament bearing material (e.g., a fabric, a gel, or a sponge), each of which can be constructed of or confined within a medically sterile material (e.g., a rigid or flexible polymer or plastic, glass, etc.). The reservoir 332 can be configured as a chamber having at least one side bound by an actuator 334 configured as a plunger 335. The plunger 335 can be configured to move inwardly to decrease an inner volume of the one or more reservoirs 332 effective to cause the one or more medicaments 331 therein to be dispensed therefrom. The plunger 335 can be advanced or retracted by pneumatic, hydraulic, piezoelectric, electromagnetic, electric motor(s), or other forces applied thereto or therefrom. For example, in an embodiment, the plunger 335 can include a hydraulic pump operably coupled thereto and configured to drive the plunger into the reservoir responsive to receiving one or more signals from the controller 112. In an embodiment, the plunger 335 can include an electric motor operably coupled thereto and configured to drive the plunger into the reservoir responsive to receiving one or more signals from the controller 112

The one or more medicaments 331 can be driven from the at least one reservoir 332 through the one or more conduits 342 by the actuator 334 (e.g., plunger 335) into and through the output apertures 344. As shown, in an embodiment, the output apertures 344 can be configured as pores 345. The pores 345 can be disposed in a selected pattern or randomly in a portion of the at least one flexible compression garment 302a. In an embodiment, each of the pores 345 can be disposed on a patch configured to be in contact with the subject. In an embodiment, each of the output apertures 344 (e.g., pores 345) is in fluid communication with the one or more reservoirs 332 such as via the at least one conduit 342 or directly with the one or more reservoirs 332 (e.g., at a distal region thereof substantially opposite the plunger 335).

In an embodiment (not shown), a medicament dispenser can include a plurality of reservoirs each having a corresponding actuator operably coupled thereto. In an embodiment, each of the plurality of reservoirs can be sized and configured to hold the same or a different volume of the one or more medicaments. In such an embodiment, the plurality of reservoirs can each contain the same or different medicaments as the other reservoirs in the medicament dispenser. In such an embodiment, the actuators can be selectively controlled by the controller to selectively deliver or direct delivery of the plurality of medicaments. For example, the controller can determine that a specific medicament is required and send a signal to the actuator of only the reservoir having the specific medicament effective to cause the actuator to manage the delivery of the medicament therefrom. Subsequent later signals can cause different or the same medicament to be delivered from the medicament dispenser responsive to different sensed data than the sensed data used to determine that delivery of the specific medicament was required. In an embodiment, a plurality of reservoirs can each include the same medicament therein, and the system can be configured to provide constant or on demand delivery of the medicament over a long period of time (e.g., days, weeks, or longer). In such an embodiment, the one or more medicaments can be delivered to the soft tissue of the subject topically or transdermally.

Figure 3B:
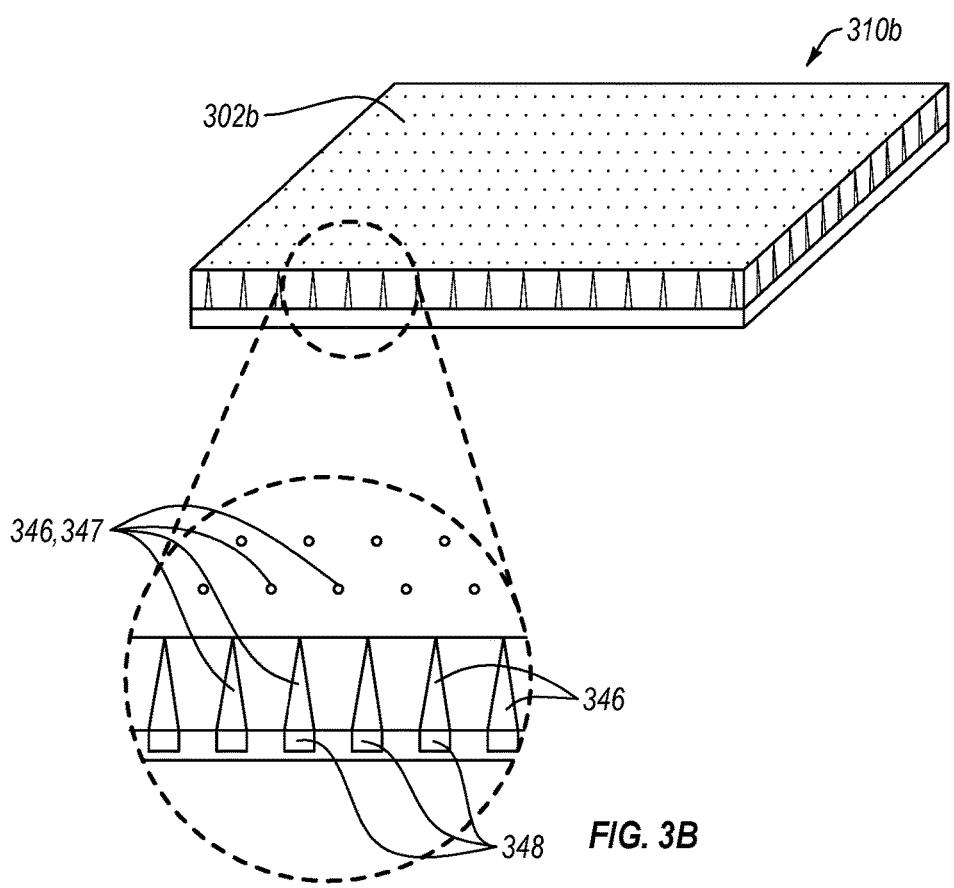
FIG. 3B is a schematic view of a medicament dispenser, according to an embodiment.

FIG. 3B is an isometric view of a medicament dispenser 310b, according to an embodiment. The medicament dispenser 310b includes a portion of the at least one flexible compression garment 302b. The medicament dispenser 310b can include one or more protrusions configured to deliver at least one medicament to the subject. The one or more protrusions can include one or more needles (e.g., a single needle). The one or more protrusions can include a plurality of micro-protrusions 346 (e.g., plurality of micro-needles or nano-needles, one or more micro-fine lances, one or more micro-fine cannulas, or one or more micro-projections), or one or more micro-jets. As shown, the one or more micro-protrusions 346 can include a plurality of micro-needles 347. The protrusions can be configured to deliver the one or more medicaments therethrough (e.g., a hollow needle structure having an output aperture operably coupled to one or more reservoirs containing a one or more medicaments). Alternatively or in addition, the protrusions can be configured to deliver the one or more medicaments incorporated thereon (e.g., a medicament incorporated on (e.g., coated) or therein (e.g., coated in an interior of a hollow protrusion or at least partially absorbed into a surface of a protrusion) and delivered via the surface of one or more protrusions. In an embodiment, the one or more protrusions can be at least partially manufactured from a dissolvable biocompatible polymer encapsulating the one or more medicaments therein. The one or more protrusions can be operably coupled to one or more actuators 348.

The one or more protrusions can enhance delivery of the one or more medicaments to or through the skin (e.g., dermal tissue), such as by placing the point of delivery or actively causing the one or more medicaments to penetrate below a stratum corneum and into a dermis of the subject, a muscle of the subject, or other soft tissue of the subject. Such systems can enhance delivery of medicaments across the dermis.

In an embodiment, the plurality of protrusions (e.g., micro-protrusions 346) can be at least partially embedded within a material of the at least one flexible compression garment 302b as shown. Prior to delivery of the medicament (or actuation of the one or more actuators), the plurality of micro-protrusions 346 can be completely embedded within the material so as not to contact or penetrate the dermis of the subject. Upon activation of the one or more actuators 348, the plurality of micro-protrusions 346 can be biased toward the skin or other soft tissue of the subject by the one or more actuators 348.

The one or more actuators 348 can be configured to selectively deliver, effect delivery, or manage delivery of the one or more medicaments. For example, the one or more actuators 348 can be operably coupled to the controller (not shown) and the one or more protrusions (e.g., micro-protrusions 346), via hardwired or wireless connections. Upon receiving one or more signals from the controller, the one or more actuators 348 can cause the one or more medicaments to be delivered to the subject through or on the one or more micro-protrusions 346. For example, the one or more actuators 348 can include one or more plungers configured to reduce an internal volume of a reservoir fluidly coupled to the one or more protrusions effective cause the one or more medicaments to travel therethrough. In an embodiment, the one or more actuators 348 can include at least one of one or more plungers, constriction elements, or expansion elements configured to cause the one or more protrusions to move in the flexible compression garment 302b toward the subject. In an embodiment, the one or more actuators 348 can be positioned and configured to cause the one or more protrusions to contact or at least partially penetrate the soft tissue of the subject, such as the dermis, a muscle, etc. In such an embodiment, the one or more medicaments can be delivered to the soft tissue of the subject topically, transdermally, intradermally, subcutaneously, or intramuscularly.

In an embodiment, the one or more actuators 348 can include a pneumatic, a hydraulic, a magnetic, an electric, an electromagnetic, or other system configured to provide a bias to a plunger or piston associated with the one or more protrusions effective to cause the one or more protrusions to contact or penetrate the soft tissue of the subject. In an embodiment, the one or more medicaments, can be incorporated (e.g., coated) on the one or more protrusions and be delivered to the subject upon contact or penetration of the skin by the one or more protrusions. For example, in an embodiment, different medicaments can be coated on different protrusions, such as on micro-needles in one or more specific regions of the flexible compression garment. In an embodiment, the one or more medicaments can be stored in one or more reservoirs fluidly coupled to the one or more protrusions and can be delivered via activation of one or more actuators 348 configured to selectively cause the one or more medicaments to move out of the reservoirs and through the one or more protrusions. In such an embodiment, the one or more medicaments can be delivered to the soft tissue of the subject topically, transdermally, intradermally, subcutaneously, or intramuscularly.

In an embodiment, a medicament dispenser includes a single needle configured to penetrate the skin of a subject. The medicament dispenser can include an actuator configured to drive the needle into the soft tissue of a subject. The medicament dispenser can further include another actuator configured to pump the medicament from a reservoir, through the needle and into the soft tissue of a subject. In such an embodiment, the controller can be programmed and configured to direct the actuators to sequentially cause the needle to insert into the subject, pump the medicament, and then retract the needle from the subject.

In an embodiment, the one or more protrusions can include a plurality of micro-jets (e.g., nanoliter-volume pulsed micro-jets) configured to deliver a high speed pulse of the one or more medicaments to the soft tissue of the subject, such as onto or at least partially through the skin of the subject. The one or more actuators can include a pressure generating system for transient mechanical, hydraulic, pneumatic, magnetic, or electrical acceleration of the one or more medicaments from the one or more micro-jets. The pressure generating system can include one or more of a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner according to a preprogramed routine stored in the controller. For example, the actuators can be configured to provide an increasing dosage of a medicament through the one or more micro-jets over a selected time period.

The one or more (high speed) micro-jets can deliver one or more medicaments by displacing the medicament solution through a micro-nozzle, e.g., 20-100 µm in final diameter. In an embodiment, the micro-nozzles can be protrusions (e.g., needles, conical structures, or polygonal protrusions, each having a channel therethrough) or substantially flat (e.g., flush) to a surface of one or more portions of the medicament dispenser or flexible compression garment. The one or more micro jets can use one or more modes of fluid displacement, such as a piezoelectric actuator displacing a plunger that provides a device or system having robustness and energy efficiency. The displacement of the plunger by the piezoelectric actuator can eject one or more micro-jets of fluid from the one or more micro-nozzles. The volume and velocity of the one or more micro-jets can be controlled by controlling the voltage and the rise time of the applied pulse to the piezoelectric actuator. At the end of the stroke, the plunger can be brought back to its original position by a compressed spring. The voltage applied to the piezoelectric crystal can be varied between 0 and 140 V to generate micro-jets with volumes up to 15 nl (e.g., about 1 nl to 15 nl, 2 nl to 15 nl, 1 nl to 5 nl, about 5 nl to about 15 nl, about 10 nl to about 15 nl) or greater than 15 nl (e.g., microliter or milliliter quantities). The frequency of pulses can be within a range of 0.1 to 10 Hz, e.g., 1 Hz. The medicament (e.g., in a liquid solution) can be filled in a reservoir, which directly feeds the solution to the micro-nozzle of the one or more micro-jets. The reservoir can be maintained at a slight overpressure, e.g., a small fraction of atmospheric pressure, to avoid backflow. In an embodiment, the piezoelectric actuator, on application of a voltage pulse, can expand rapidly to push a plunger that ejects the fluid from the micro-nozzle as a high-speed micro-jet.

In an embodiment, piezoelectric crystal actuators expand when electrically activated to drive small liquid volumes (e.g., 10-15 nl) through a micro-jet (e.g., a micro-nozzle therein) at high speed (greater than about 100 meter/sec). The high speed of the micro-jets allows their entry into the skin (e.g., dermal tissue), whereas the small jet diameters (20-100 µm) and extremely small volumes (2-15 nl) limit the penetration depth (~200 µm).

The volume of the micro-jet is proportional to the amplitude of the voltage pulse, and the velocity of the micro jet is proportional to the rise time. In further detailed aspects, a rise time of 10 µseconds would lead to a mean velocity of 127 meters/second for a 10-nanoliter micro-jet delivered from a 100-µm diameter micro-nozzle. For example, $v=Q/At$, where Q is the micro-jet volume, A is the cross-sectional area of the micro-nozzle, and t is the rise time. By controlling the amplitude and rise time of the pulse, velocity as well as volume of the micro jet can be adjusted. Dispensed volume from the nozzle is replaced by liquid from the reservoir, which is maintained under slight positive pressure to avoid backflow.

Under typical operating conditions, micro-jets can be ejected from the micro-nozzle(s) at exit velocities of at least 100 meters/second and volumes of about 10 to about 15 nanoliters. The micro-jets can be cylindrical in shape and each jet pulse could be clearly distinguished. To deliver volumes in excess of about 10 to about 15 nanoliters, the micro-jets can be designed to operate over a prolonged time period, and the total amount of medicament ejected will be proportional to the application time. In an aspect, a pulsation frequency of 1 Hz (1 microjet per second) can be used. This frequency can be increased if higher delivery rates are desired. Other modes of fluid displacement to provide high speed micro jets include dielectric breakdown, electromagnetic displacement, springs, solenoids, motors, or compressed gas actuators.

In an embodiment, the at least one flexible compression garment 302b can include multiple layers extending substantially parallel to one another. In an embodiment, one or more of the one or more protrusions or one or more actuators 348 can be disposed in (e.g., at least partially embedded within) adjacent layers. In an embodiment, one or more of the one or more protrusions or one or more actuators 348 can be disposed in the same layer.

Figure 3C:
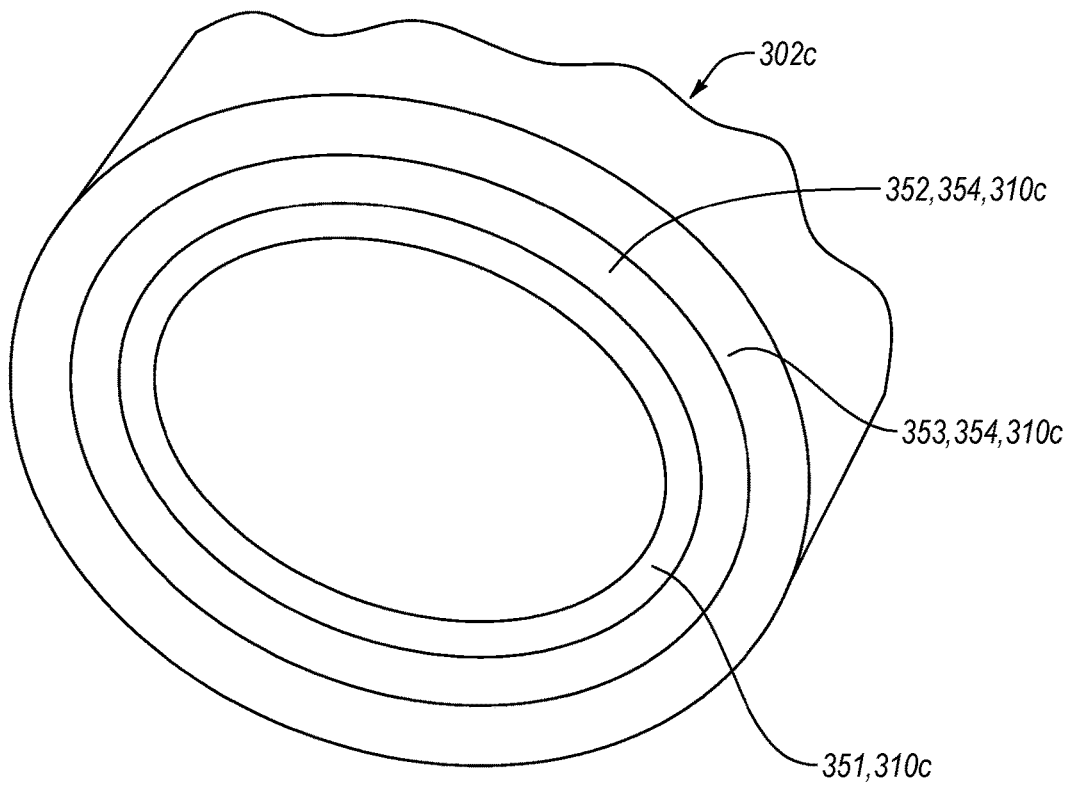
FIG. 3C is an isometric view of a portion of a flexible compression garment, according to an embodiment.

As shown in FIG. 3C, in an embodiment, the a medicament dispenser 310c having one or more actuators can be positioned relative to the flexible compression garment 302c and configured to cause one or more portions of the flexible compression garment 302c to selectively constrict or selectively dilate at (e.g., around) one or more portions of the flexible compression garment 302c, thereby selectively causing the delivery of one or more medicaments in the associated medicament dispenser to the subject. Such selective delivery can be responsive to the one or more signals output by the controller (not shown). For example, a medicament dispenser 310c (e.g., one or more actuators 354) can be at least partially embedded in the flexible compression garment 302c, mounted interiorly inside at least a portion of the flexible compression garment 302c in an interior space thereof in which the at least one body part is received, or mounted exteriorly on at least a portion of the flexible compression garment 302c.

In an embodiment, the flexible compression garment 302c can include one or more layers extending substantially parallel to one another. In such an embodiment, any of the one or more protrusions, reservoirs, conduits, actuators, delivery orifices, or other portions of the medicament dispensers disclosed herein can be disposed on, in (e.g., embedded within), or between the one or more layers. For example and as shown in FIG. 3C, the one or more layers can include a first layer 351 disposed at least partially interiorly to the remaining layers 352 and 353, a second layer 352 disposed at least partially between at least a portion of the remaining layers 351 and 353, and a third layer disposed at least partially exteriorly to the remaining layers 351 and 352.

In an embodiment, the one or more micro-protrusions 346 disclosed above can be disposed within the first layer 351 or the second layer 352 and the third layer 353 can include at least one actuator 354 configured to cause the third layer to selectively constrict or dilate effective to control the bias of the micro-protrusions 346 into or away from the subject. For example, the first layer can include a soft material such as neoprene, the second layer can include a plurality of medicament coated micro-protrusions 346, and the third layer 353 can include an actuator 354 configured as a fluid reservoir having an inner volume configured to expand or collapse upon ingress or egress of a fluid therein via activation of the actuator 354 by the controller (not shown). The expansion or collapse of the inner volume can cause the one or more micro-protrusions 346 to be biased through the first and second layers 351 and 352 so as to contact or penetrate the soft tissue of the subject, thereby delivering the one or more medicaments to the subject.

In an embodiment (not shown), one or more pores can be disposed within the first layer 351, the second layer 352 can include one or more reservoirs containing one or more medicaments therein (e.g., a fluid containing bag or a medicament soaked porous material), and the third layer 353 can include an actuator 354 configured to cause the third layer to selectively constrict or dilate effective to control the internal volume of the one or more reservoirs. For example, the first layer 351 can include a material having one or more pores therein, the second layer 352 can include a reservoir fluidly connected to the one or more pores, and the third layer 353 can include an actuator 354 configured to expand or collapse the inner volume of the at least one flexible compression garment (as measured from the outer surface thereof) effective to cause the one or more medicaments to be forced from the one or more reservoirs through the plurality of pores and onto the subject via the inward pressure exerted from the one or more actuators 354. The one or more actuators 354 can be selectively directed to manage (e.g., initiate, increase, maintain, decrease, or cease) the delivery of the one or more medicaments via one or more signals from the controller (not shown).

In an embodiment, each of a plurality of reservoirs can include a different or the same medicament and each of the plurality of reservoirs can have a corresponding actuator 354 configured to cause delivery of the medicament only from the corresponding reservoir. Such individual reservoirs and actuators 354 can be located in distinct regions of the flexible compression garment. In such an embodiment, each of the plurality of reservoirs can be selectively directed by the controller to selectively manage delivery of the medicament therefrom. Such selective delivery can be separate, sequential, or simultaneous. Such selective delivery can be according to a preprogrammed routine.

The one or more actuators 354 can be selected from a number of suitable different types of actuators. The one or more actuators 354 can include at least one of one or more electroactive polymer actuators, one or more electroactive metallic actuators, one or more thermally active polymer actuators, one or more motors, one or more fluid displacement actuators (e.g., one or more hydraulic actuators or one or more pneumatic actuators), one or more plungers, one or more gear systems, or any other suitable actuators. Any of the actuators disclosed herein can be used in any of the embodiments of the systems described herein. Additionally, any of the one or more actuators (e.g., actuators 354) can be arranged in any of a number of different configurations or positions in a system.

In an embodiment, the one or more actuators 354 include one or more electroactive polymer actuators. In an embodiment, the one or more electroactive polymer actuators include one or more actuator elements at least partially formed from ferroelectric polymers, dielectric elastomers, or electrostrictive graft elastomers. Responsive to a voltage or current applied by a power source and based on a signal (e.g., instructions) from the controller (not shown), the electroactive polymer actuators can increase or decrease in length, diameter, or other dimension depending on the polarity of the applied voltage to cause one or more portions of the flexible compression garment 302c to selectively constrict or dilate. For example, suitable electroactive polymers for the electroactive polymer actuators include at least one of NuSil CF19-2186 commercially available from NuSil Technology of Carpinteria, Calif., silicone elastomers, acrylic elastomers (e.g., VHB 4910 acrylic elastomer commercially available from 3M Corporation of St. Paul, Minn.), polyurethanes, thermoplastic elastomers, copolymers including polyvinylidene difluoride (PVDF), pressure-sensitive adhesives, fluoroelastomers, polymers including silicone and acrylic moieties, or other suitable electroactive polymers.

In an embodiment, the one or more electroactive metallic actuators include one or more actuator elements at least partially formed from a shape memory material. For example, the shape memory material can include a nickel-titanium shape memory alloy, such as nitinol or other suitable nickel-titanium alloy composition. Responsive to the power source passing a current through the shape memory material to heat the shape memory material based on instructions from the controller, the electroactive metallic actuators can increase or decrease in length, diameter, or other dimension depending on the temperature to which the shape memory material is heated to cause at least a portion of the flexible compression garment 302c to selectively constrict or dilate.

Examples of such nickel-titanium shape memory alloys are currently commercially available from Dynalloy, Inc. and sold under the trade name Flexinol®. Flexinol HT® has a transition temperature of about 194° F., with an activation start temperature at about 190° F. and an activation finish temperature at about 208° F. Such nickel-titanium alloys can gradually and controllably contract in length about 2% to about 5% of their length or other dimension as they are heated from the activation start temperature to the activation finish temperature.

In an embodiment, the one or more actuators 354 include one or more thermally active polymer actuators. In an embodiment, the one or more thermally active polymer actuators can include one or more actuator elements at least partially formed from temperature-responsive polymers, such as polyester, polyurethane, polypropylene, polyethylene, or nylon. Responsive to heat or change in temperature applied by the power source based on instructions from the controller, the thermally active polymer actuators can increase or decrease in length, diameter, or other dimension depending on the temperature change to cause at least a portion of the flexible compression garment 302c to selectively constrict or dilate. For example, suitable temperature responsive polymers for the thermally active polymer actuators include at least one of a polyester, a polyurethane, a polypropylene, a polyethylene (e.g., polytetrafluoroethylene), nylon, or other suitable temperature responsive polymers.

In an embodiment, the one or more actuators 354 include one or more motors. In an embodiment, the one or more motors include one or more micro-electro-mechanical actuators. For example, the one or more micro-electro-mechanical motors can include one or more micro-piezoelectric actuators, one or more micro-electrostatic actuators, or one or more micro-electromagnetic actuators. One suitable micro-piezoelectric actuator is New Scale's SQUIGGLE™ motor. Such motors can be configured to move plungers, move gears, move micro-protrusions, etc.

In an embodiment, the one or more actuators can include one or more constriction actuators or elements. The one or more constriction actuators can be configured to increase or decrease an interior space of at least a portion of the flexible compression garment. In an embodiment, the one or more constriction actuators extend circumferentially about a substantially tubular flexible compression garment and can be configured to reduce a radial cross section of at least a portion of the flexible compression garment. In an embodiment, the one or more constriction actuators can be a plurality of substantially ring-shaped actuators. In an embodiment, one or more constriction actuators can extend around one or more reservoirs and be configured to constrict around the one or more reservoirs effective to cause a fluid therein to move out of the reservoir. Some constriction actuators can include one or more of electroactive polymer actuators, gear systems, electroactive metallic actuators, thermally active polymer actuators, one or more motors, hydraulic actuators, pneumatic actuators, piezoelectric actuators, one or more plungers, etc.

In an embodiment, the one or more actuators 354 include a gear system configured to constrict or dilate (e.g., tighten or loosen) the at least a portion of the at least one flexible compression garment 302c. For example, the gear system can include a reel having gears therein and lacing connected therethrough. The gear system can be similar or identical to the Boa Closure System sold by Boa Technology, Inc. of Denver, Colo. or similar system. The gear system can be operably coupled to a motor configured to cause the gear system to tighten or loosen the lacing connected to the reel. The lacing of the gear system can extend circumferentially or longitudinally through at least a portion of the flexible compression garment 302c. Responsive to receiving a signal from the controller, the motor of the gear system can tighten or loosen the lacing therein, thereby constricting or dilating at least a portion of the flexible compression garment 302c circumferentially or longitudinally without manual manipulation.

In an embodiment, the one or more actuators 354 can include a pneumatic system (e.g., a compressed gas system) configured to selectively constrict or selectively dilate at least a portion of the flexible compression garment 302c. The compressed gas system is configured to provide inflow of compressed gas into or outflow of the compressed gas from at least a portion of the at least one flexible compression garment 302c. For example, the flexible compression garment 302c can include one or more discrete, air-tight, chambers extending circumferentially or longitudinally therethrough, such as in the second or third layers 352 or 353 of FIG. 3C. Each of the discrete chambers can be fluidly connected to a source of compressed gas, such as a compressed gas cylinder having a regulator connected thereto. In an embodiment, responsive to receiving the actuation signal from the control electrical circuitry, the compressed gas system can cause the regulator to allow inflow of gas from the cylinder into one or more of the discrete, air-tight chambers thereby constricting at least a portion of the flexible compression garment 302c (e.g., a portion around a reservoir or a portion configured to apply a bias one or more micro-protrusions). In an embodiment, responsive to receiving the signal from the controller, the compressed gas system can cause the regulator or valve connected to one or more of the discrete, air-tight chambers to open thereby dilating the flexible compression garment 302c. A similar or identical configuration can be used in a hydraulic system.

Figure 3D:
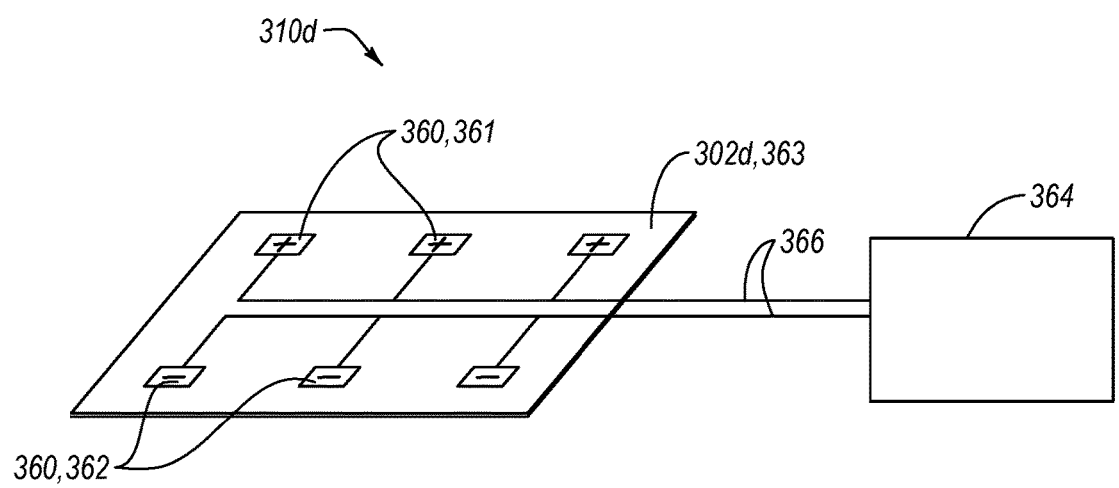
FIG. 3D is a schematic view of a medicament dispenser, according to an embodiment.

FIG. 3D is a schematic view of a medicament dispenser 310d configured as an iontophoretic device, according to an embodiment. In such an embodiment, the medicament dispenser 310d can include a plurality of electrodes 360, a medicament source (e.g., medicament containing material 363) in contact with the plurality electrodes 360, and a power source 364. The plurality of electrodes 360 can include one or more first electrodes 361 and one or more second electrodes 362. Each of the plurality of electrodes 360 can be disposed on the same portion of a material 363, such as on the same region of the at least one flexible compression garment 302d or a patch, or can be disposed on different portions of the material 363. The material 363 can include one or more medicaments therein, such as soaked therein. The material 363 can be a porous material capable of retaining a medicament (e.g., a fluid) therein. Each of the plurality of electrodes 360 can be electrically coupled to a power source 364 via wiring 366. The power source 364 can be configured to selectively and independently deliver current through or apply a voltage to the one or more electrodes 360 responsive to one or more signals from the controller (not shown). The plurality of electrodes 360 are disposed on the material 363 effective to maintain or bring the plurality of electrodes 360 into electrical communication with the subject.

In an embodiment, the material 363 can include a plurality of medicaments therein (e.g., in different regions thereof) and the plurality of electrodes 360 can include at least one first electrode 361 and at least one second electrode 362 adjacent to each of the plurality of medicaments. Responsive to one or more signals from the controller, the power source 364 can selectively control the application of current or voltage to specific electrodes 360 to manage the delivery of selected medicaments. Upon application of current or voltage, the one or more medicaments can be delivered via ionic diffusion at least partially through the skin facilitated by the electric field supplied by the power source 364 and electrodes 360. The selective delivery can be based at least in part on the region that the medicament is disposed in or on the type of medicament required. In an embodiment, one or more specific sensors can be associated with (provide the sensed data for determination of dispensing requirements) the delivery of a specific medicament or a medicament in a specific region of the at least one flexible compression garment. In such an embodiment, the medicament dispenser is configured to at least selectively transdermally deliver one or more medicaments, such as in one or more regions.

In an embodiment, the medicament dispenser can include one or more electrodes on or in electrical communication with any of the one or more projections disclosed above. In such an embodiment, the one or more electrodes or one or more projections (e.g., a plurality of micro-projections) are configured to apply electrical energy to skin of the subject. The electrodes and projections can provide ablation of stratum corneum in an area beneath the electrodes thereby generating a plurality of hydrophilic micro-channels in the skin of the subject. The hydrophilic micro-channels can be used to deliver one or more medicaments through or on the projections.

In an embodiment, the one or more actuators can also include one or more heating or cooling devices. In such an embodiment, responsive to the one or more signals from the sensors, the controller can be configured to direct the one or more actuators to additionally or alternatively heat or cool a region of the subject.

In an embodiment, the one or more medicament dispensers (e.g., the one or more medicament dispensers 110 shown in FIG. 2D) include one or more energy sources. Each of the one or more energy sources can include an electrical source (e.g., electrodes), a thermal source, or a light source. For example, a thermal source (e.g., a thermal coil) can provide heat to the skin of the subject to aid in enhancing transdermal delivery of a medicament. A light source (e.g., one or more light-emitting diode) can provide light to a body part, including light of a particular wavelength. For example, a light source can provide light to a body part to activate a photo-activatable drug. For example, a light source can provide a blue light (e.g., 465-475 nm wavelength) to induce vasodilation to enhance uptake of a drug. In an embodiment, a light source can provide light for phototherapy. For example, the light source can provide light, such as blue light (e.g., to the back of the knee), to aid in treatment of a disorder (e.g., depression) in addition to or as an alternative to a drug regiment (e.g., a vitamin cocktail). For example, an electrical source (e.g., an electrode) can deliver energy to a body part. For example, one or more electrodes can deliver electrostimulation to the skin to aid in drug delivery. For example, the one or more electrodes can deliver a stimulus to a tissue, such as the one or more electrodes can deliver the stimulus transcutaneously to a nerve or a muscle. For example, the one or more electrodes can include a transcutaneous electric nerve stimulation (TENS) unit.

In any of the embodiments herein, any of the one or more sensors or actuators can be microscale or nanoscale, such as including a microelectromechanical device.

Figure 4:
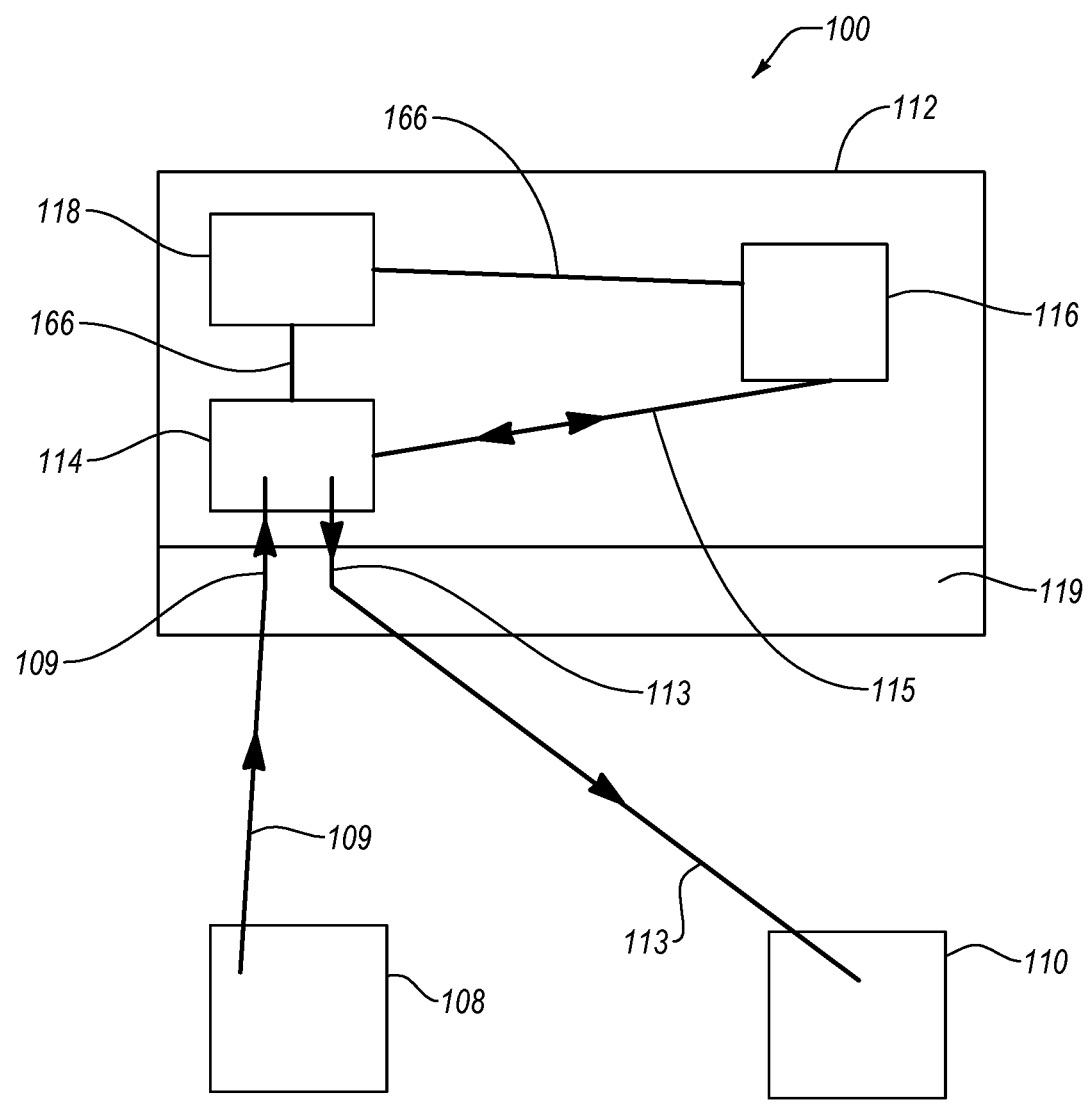
FIG. 4 is a block diagram of a portion of a system for dispensing medicaments including a controller, according to an embodiment.

FIG. 4 is a block diagram of a portion of the medicament delivery system 100, according to an embodiment. As discussed above, the controller 112 can be operably coupled to the one or more sensors 108 and the one or more medicament dispensers 110. For example, the controller 112 can be wirelessly coupled to the one or more sensors 108 or the one or more medicament dispensers 110. In an embodiment, the controller 112 can be operably coupled to the one or more sensors 108 or the one or more medicament dispensers 110 via a wired connection, such as physical electrical wiring. The controller 112 can be sized and configured to be conveniently worn or carried by the subject 106, such as in or on the flexible compression garment (not shown) or wearable device 107 (not shown). In an embodiment, the controller 112 can be disposed on yet another body part such as in or on another wearable device (e.g., a strap, wrap, article of clothing, garment, or belt) worn around a waist, chest, arm, hand, leg, foot, or head, of the subject. In any of the embodiments, the controller 112 can be mounted on, attached to, embedded in, or housed in the flexible compression garment or a wearable device. In an embodiment, the controller 112 can include or be a remote device separate from the flexible compression garment and the wearable device. For example, the remote device can include a computer (e.g., a desktop or laptop computer), a tablet, a smartphone, a communication device, or another electronic device. The remote device can be accessed and used by the subject or another person, such as a medical professional.

The controller 112 can include a processor 114 including processing electrical circuitry, memory 116 including memory electrical circuitry, and a power source 118. In an embodiment, the controller 112 can include an interface 119 operably coupled thereto and configured to communicate with and receive sensed data 109 from the one or more sensors, signals 113 from the processor, or input from a user (e.g., the subject or medical professional). The processor 114 can be configured to receive sensed data 109 from one or more sensors 108 and determine if the sensed data 109 indicates a change (e.g., initiation, increase, decrease, or termination) or maintenance of the current delivery state of the one or more medicaments is required. The processor 114 can access the memory 116 via an operable connection 115 therebetween. The operable connection 115 can be a wireless connection (e.g., Bluetooth, Wi-Fi, infrared beams, etc.) or hardwired connection. The processor 114 can receive and process the one or more sensed signals 109 (e.g., as relayed through the interface 119). The processor 114 can send the sensed or processed data to the memory 116 for storage via the operable connection 115.

The memory 116 can include a hard disk drive (e.g., magnetic or optical memory storage), solid state memory device, virtual or cloud based memory storage, or any other memory device. The processor 114 can access stored data in the memory 116 for use in processing or other operations. Stored data can include stored sensed data 109, look-up tables, programs (e.g., pre-programmed programs), actuation data corresponding to the selective delivery of one or more medicaments, threshold levels, or other data related to the operation of the system 100 or health care of the subject 106. The stored data can be used to determine if sensed data 109 indicates that a change or maintenance in a delivery state of the one or more medicament dispensers 110 is required. For example, the stored data can include a look-up table which is accessed by the processor 114 to determine if the sensed data 109 indicates that a threshold condition has been met or exceeded. The stored data can include look-up tables or other information (e.g., physiological, environmental, or other information) related to one or more specific subjects or one or more demographics that a subject can be included in. In other embodiments, the stored data can include a program configured to direct the delivery of the one or more medicaments according to the program instructions therein. Such program instructions can include which sensed physiological conditions, threshold conditions or levels, environmental conditions, or other conditions require dispensing a medicament; which medicament(s) should be dispensed based on the sensed data; how much of the one or more medicaments should be released based on the sensed data; and if multiple doses or timed release of the one or more medicaments is appropriate.

Responsive to the processor 114 determining if a change or maintenance of a delivery state is required, the processor 114 can selectively output one or more signals 113 to the one or more medicament dispensers 110. Each signal 113 is configured to direct the one or more actuators therein (not shown) to selectively manage delivery of the one or more medicaments in the one or more medicament dispensers 110. In an embodiment, the one or more signals 113 can be relayed through the interface 119. In an embodiment, the one or more signals 113 can be sent directly from the processor 114 to the one or more medicament dispensers 110 or actuators therein.

In an embodiment, the controller 112, one or more sensors 108, and one or more medicament dispensers 110 are configured to actively monitor one or more sensed data and actively control the selective delivery of the one or more medicaments based thereon. In such an embodiment, the amount or types of medicaments can be actively maintained or changed over time based on one or more changing or static physiological, environmental, or other conditions of the subject.

The power source 118 can be electrically coupled (e.g., hard-wired or wirelessly coupled to) to and configured to provide power (e.g., voltage or current) to one or more of the processor 114, the memory 116, the interface 119, the one or more sensors 108, or the one or more medicament dispensers 110. The power source 118 of the controller 112 can include at least one of one or more batteries, a stretchable/flexible power source, a fuel cell, an energy harvester, a solar energy harvester (e.g., solar cells), a kinetic energy harvester (e.g., motion-activated generator), a triboelectric nanogenerator, a wired power source (e.g., a wall outlet), or other suitable power source. In an embodiment, the power source 118 can be housed separately from one or more of the other components of the controller 112. Suitable batteries for use as the power source 118 include one or more of a microbattery, an alkaline battery, a lithium ion battery, a coin battery, a watch battery, a button battery, a zinc-air battery, a thin film battery, a flexible battery, or any other suitable battery.

In an embodiment, the power source 118 can be stored or housed separately from the controller 112. In an embodiment, the one or more the processor 114, the memory 116, the interface 119, the one or more sensors 108, or the one or more medicament dispensers 110 can have an individual power source stored therein or otherwise associated therewith (e.g., stored in the controller 112 or another portion of the system 100). In an embodiment the power source 118 can be stored or housed on a separate part of the body of the subject 106 than the controller 112, one or more medicament dispensers 110, or one or more sensors 108, wearable device 107, or at least one flexible compression garment 102. In an embodiment, the power source 118 can include a wireless power source, such as a power source configured to supply power via induction (e.g., direct or resonant magnetic induction).

In an embodiment, the power source 118 is rechargeable. For example, a wearable device 107 can include a charging port operably coupled to the power source 118 and configured to recharge the power source 118.

One or more of the sensors, medicament dispensers (e.g., actuators), or interface can include a power supply operably coupled thereto, such as therein or wired thereto. In an embodiment, each of the sensors or actuators can be operably coupled to a single power supply. In an embodiment, each of the sensors and medicament dispensers (e.g., actuators) can include a battery operably coupled thereto (e.g., therein), respectively.

The interface 119 can be configured to communicate with one or more of the one or more sensors 108, the one or more medicament dispensers 110, processor 114, the memory 116, or remote devices (not shown) such as a tablet, computer, personal communication device (e.g., smartphone), or remote control device. In an embodiment, in addition or alternatively to the processor 114 determining if the sensed data is indicative of a condition that requires dispensing of one or more medicaments and sending a signal to direct the one or more medicament dispensers, the determination or signal can be carried out by the remote device. For example, the determination can be carried out in a personal computer operably coupled to the controller via the interface 119. In an embodiment, the remote device can be used to provide programming or instructions to the controller 112.

While shown as being physically attached to the controller 112, in an embodiment the interface 119 is operably coupled to or located on a remote device, such as a cellular phone, a desktop computer, a tablet computer, a laptop computer, an external switch, or a remote control. In an embodiment, the interface 119 can act as a relay for signals between any of the above components. In an embodiment, the interface 119 can be configured as a user input device or user interface. In such an embodiment, the interface 119 can include a user input device capable receiving user input of data or commands (e.g., programming instructions or control instructions) into the processor 114 or memory 116. The user input device can include a keyboard, a touchscreen, wireless connection (e.g., Bluetooth connection or Wi-Fi connection), memory disk port, USB port, voice command receiver, or any other connection capable of transferring data into the memory 116 or commands to the processor 114. In such an embodiment, the interface 119 can be used to provide program or pre-program the processor 114 or the memory 116 with program instructions or control instructions, such as via the USB port, wireless connection, or keyboard. In an embodiment, the interface 119 can be used to adjust or set the criteria by which the processor 114 determines that the one or more medicaments need to be dispensed. For example, the interface 119 can be used to set, lower, raise or otherwise adjust one or more threshold levels of a sensed physiological characteristic of the subject. In an embodiment, the interface 119 can include one or more buttons, switches, dials, or toggles, configured to cause the processor 114 to immediately direct the one or more medicament dispensers 110 to selectively manage the delivery of the one or more medicaments according to the user input (e.g., a button for initiation or increase of medicament delivery). For example, in such an embodiment, the one or more sensors 108 can be omitted, if desired.

In an embodiment, the interface 119 can include at least one reporting device for communicating with a user (e.g., the subject or a medical professional) such as a screen, an alpha-numeric display, a haptic device (e.g., vibration), heating or cooling, one or more lights, or one or more sound generation devices (e.g., speakers or chimes). In such an embodiment, the processor 114 can be configured to send a signal to the interface 119 effective to cause the interface 119 to display or otherwise make a user or subject aware of a delivery state of the one or more medicament dispensers or medicaments, the status of the system 100 (e.g., functioning properly, power state, which medicaments are contained therein and where they are disposed on the subject), the condition of the subject based on the sensed data 109 (e.g., a report with sensed data/information from one or more of the sensors 108), that a condition indicative of the need to dispense a medicament has been detected and determined by the system, the timing or amount of at least one of the one or more medicaments that was delivered to the subject or the timing or amount that will be delivered to the subject, status of a program that is currently running and contents of the program, or any other information the user can find useful with respect to the system 100.

The controller 112, processor 114, memory 116, or interface 119 can be accessed or controlled locally (e.g., directly by the subject or a person within reach of the subject) or remotely (e.g., by a coach, trainer, doctor, medical professional, or other person located outside of arms reach of the subject). During operation, the processor 114 accesses and receives instructions (e.g., operational programs) from the memory 116 and directs the sensing operations of the one or more sensors 108 and control of the one or more medicament dispensers (e.g., one or more actuators therein) at least partially based on the instructions. For example, responsive to the instructions stored in the memory 116, the processor 114 can direct the one or more actuators in the one or more medicament dispensers 110 to dispense one or more medicaments, which can be responsive to the sensed data 109 detected by the one or more sensors 108 and processed by the processor 114.

During use in some operational situations, responsive to the one or more sensors 108 sensing the at least one characteristic associated with movement of the subject 106 or at least one physiological characteristic of the subject 106, the controller 112 can be configured to direct the one or more medicament dispensers 110 (e.g., actuators therein) to selectively manage delivery of the one or more medicaments to the at least one body part 104 or region of the at least one body part. For example, responsive to the one or more sensors 108 sensing, and the processor 114 determining that the least one physiological characteristic of the subject 106 is above (or below) a threshold level, the controller 112 is configured to direct the one or more actuators (FIGS. 3A-3D) to selectively manage delivery of the one or more medicaments.

For example, in an embodiment, the controller 112 (e.g., processor 114) is configured to determine if a body part of the subject is fatigued (e.g., via a comparison one or more sensor data over time indicative of a slowing pace or activity level, or by detecting a depletion of chemical components in a body fluid), swollen (e.g., via localized pressure applied to one or more sensors), injured, or strained (e.g., sensor data indicating that the subject is favoring a body part). Responsive to the determination, the controller 112 (e.g., processor 114) is configured to send a signal 113 to direct the one or more actuators (not shown) in the one or more medicament dispensers 110 to selectively manage delivery of the one or more medicaments.

The controller 112, one or more sensors 108, or one or more medicament dispensers 110, including any parts thereof, can be configured to be removably disposed on the at least one flexible compression garment 102 or wearable device 107. For example, one or more of the controller 112, the one or more sensors 108, or the power source 118 can be configured in a modular format, such as replaceable or changeable sensors 108.

One or more of the controller 112, the one or more medicament dispensers 110, or the one or more sensors 108 can be configured to directly or indirectly interface with a computing device. For example, the controller 112 can be configured to be removably disposed on the wearable device 107, and the controller 112 is also configured to interface, either directly or indirectly, with a computing device, such as by a hard connection (e.g., USB connection) or wireless port on the thereon. In an embodiment, at least one of the controller 112 or the one or more sensors 108 are further configured to upload or download one or more of at least one operational program, threshold level, or sensed data to or from the computing device. The one or more operational programs that the processor 114 in the controller 112 employs for directing and controlling the operation of the one or more sensors 108 and the one or more actuators can be pre-programmed in the controller 112, or programmed by the subject 106 or other person such as a medical professional like a doctor, a nurse, a physical therapist, a trainer, etc. For example, the programming of the controller 112 can be affected via at least one of software, firmware, programmable logical devices, or other technique. As noted above, programming of the controller 112 can be affected via the interface 119.

In an embodiment, the subject or other user (e.g., a caregiver), can provide user input via the interface 119 via the user input device. For example, the user input can direct the controller 112 to direct delivery of the one or more medicaments from the one or more medicament dispensers 110.

In an embodiment, the one or more sensors 108 can report to the subject or other user via the interface 119 sensing data sensed by the one or more sensors 108. At least partially based on the reported sensing data, the subject or other user can direct the controller 112 to direct delivery of the one or more medicaments from the one or more medicament dispensers 110. In other embodiments, the one or more sensors 108 can be omitted and operation of the controller 112 can be responsive solely to programming or input from the subject or other user.

Figure 5A:
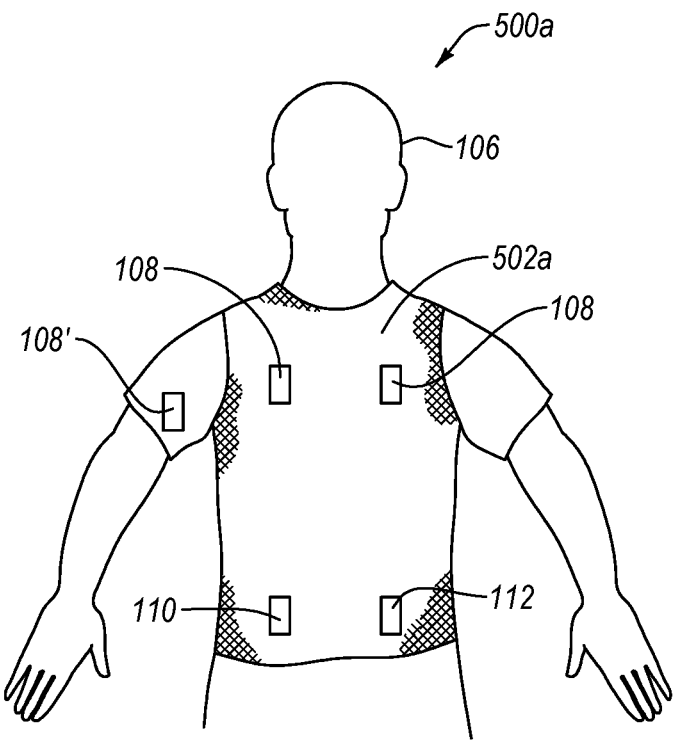
FIG. 5A is a schematic view of a system for dispensing medicaments, according to an embodiment.
Figure 5B:
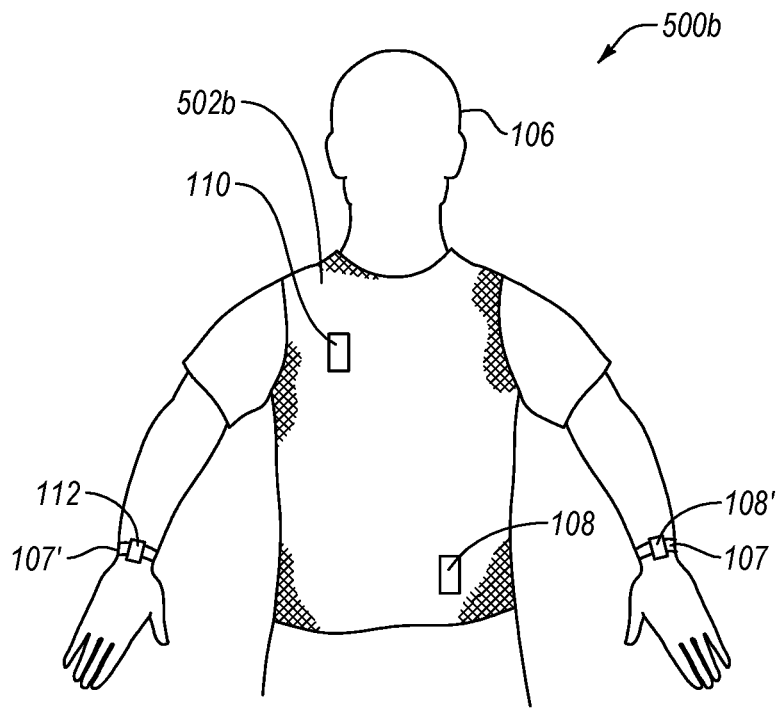
FIG. 5B is a schematic view of a system for dispensing medicaments including one or more wearable devices, according to an embodiment.
Figure 5C:
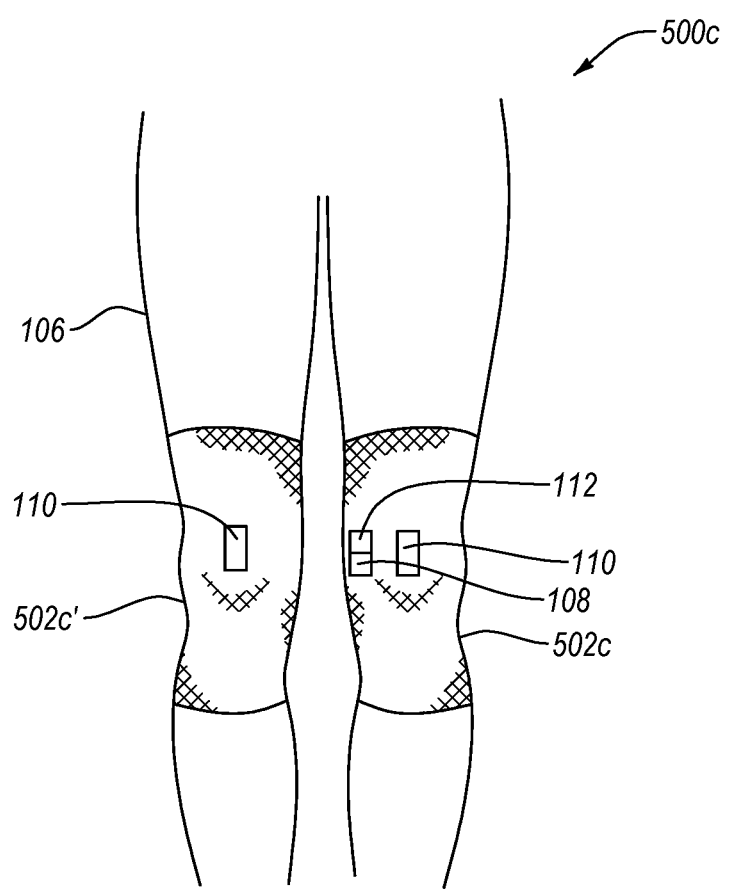
FIG. 5C is a schematic view of a system for dispensing medicaments including a more than one flexible compression garment and medicament dispenser, according to an embodiment.

The systems disclosed herein, or portions thereof can be worn in various configurations on various body parts of the subject 106. FIGS. 5A-5C are schematic views of medicament dispensing systems on a subject according to various embodiments.

In an embodiment, each of the one or more sensors 108 or 108', one or more medicament dispensers 110, and controller 112 can be disposed on or in the same flexible compression garment. FIG. 5A is a schematic view of a system 500a, according to an embodiment. The medicament dispensing system 500a includes a flexible compression garment 502a configured as a shirt and having a plurality of sensors 108 and 108' therein. The flexible compression garment 502a includes one or more medicament dispensers 110 therein. The flexible compression garment 502a includes a controller 112 therein. The one or more sensors 108 or 108' can be similar or identical to any sensor disclosed herein. The controller 112 can be similar or identical to any controller disclosed herein. The one or more medicament dispensers 110 can be similar or identical to any medicament dispenser disclosed herein.

The one or more sensors 108 or 108' can be disposed on one or more regions of the flexible compression garment 502a configured to detect a specific physiological characteristic or data related thereto or from a body part therein or adjacent thereto. The body part can be any body part disclosed herein. For example, one or more sensors 108 can be disposed on the torso (e.g., near the lungs or heart) to detect data related a heart rate, sinus rhythm (e.g., acoustic data), breathing rate (e.g., acoustic data), or breathing rhythm. As shown, one or more sensors 108' can be disposed on an arm, such as to detect a motion, strain, pulse in an extremity, or chemical in a body fluid excreted therefrom. The controller 112 can be disposed in the at least one flexible compression garment 502a. The controller 112 can be positioned in a portion of the flexible compression garment configured to be accessible to a subject 106 or in a region of the flexible compression garment configured to undergo the least impact or jarring.

In an embodiment, one or more of the controller 112, one or more medicament dispensers 110, or one or more sensors can be disposed in separate articles. FIG. 5B is a schematic view of a system 500b. The medicament dispensing system 500b includes a flexible compression garment 502b having a plurality of sensors 108 and 108' therein and one or more wearable devices 107 and 107' having one or more sensors 108, one or more medicament dispensers (not shown), or a controller thereon, respectively. The flexible compression garment 502b can be configured as any flexible compression garment disclosed herein, such as a shirt. The flexible compression garment 502b includes one or more medicament dispensers 110 therein. The one or more sensors 108 or 108' can be similar or identical to any sensor disclosed herein. The controller 112 can be similar or identical to any controller disclosed herein. The one or more medicament dispensers 110 can be similar or identical to any medicament dispenser disclosed herein.

The one or more sensors 108 can be disposed on one or more regions of the flexible compression garment 502b configured to detect a specific physiological characteristic or data related thereto, or from a body part therein or adjacent thereto. The body part can be any body part disclosed herein. For example, one or more sensors 108 can be disposed on the torso (e.g., near the stomach or kidneys) to detect data related a movement or chemical composition of body fluid(s) adjacent thereto. As shown, one or more sensors 108' can be disposed on a wearable device 107 disposed on an additional body part of the subject than the body part in flexible compression garment 502b. The additional body part can be any body part disclosed herein. For example, the wearable device 107 can be configured as a wristband having the one or more sensors 108' and can be worn on the wrist of the subject 106, such as to detect a motion, strain, pulse in an extremity, or chemical in a body fluid excreted therefrom. The system 500b can include another wearable device 107' disposed on any body part of the subject separate from the those body parts having the wearable device 107 and the flexible compression garment 502b thereon. The controller 112 can be disposed in the wearable device 107'. The wearable device 107' and the controller 112 can be positioned on a body part of the subject 106 that is accessible to the subject 106 (e.g., an interface on the controller 112 can be readily viewed or manipulated) or a body part or region thereon predicted to undergo the least impact or jarring. For example, the wearable device 107' can be worn on the other wrist of the subject 106, such as in the form of a wrist wrap or bracelet.

In an embodiment, the wearable device 107 or 107' can be removably or reusably worn on any of multiple body parts of the subject 106. For example, the wearable device 107' can be configured as a wrist band having an adjustable strap thereon, wherein the adjustable strap can be adjusted out to allow the wrist band to fit around a portion of the leg of the subject, or around the head of the subject 106.

In an embodiment, more than one compression garment can be used, and one or more of the controller 112, one or more medicament dispensers 110, or one or more sensors can be disposed in one or each of the flexible compression garments. FIG. 5C is a schematic view of a system 500c. The medicament dispensing system 500c includes a flexible compression garment 502c and a flexible compression garment 502c'. The flexible compression garments 502c and 502c' can be configured to be worn on and conform to different body parts such as complementary body parts like both knees as shown in FIG. 5C. In an embodiment, one or both of the flexible compression garments 502c and 502c' can include one or more sensors 108, one or more medicament dispensers 110, or a controller 112 thereon, respectively. For example and a shown, the flexible compression garment 502c can include one or more sensors 108, one or more medicament dispensers 110, and the controller 112 thereon; and the flexible compression garment 502c' can include one more medicament dispensers 110 thereon. In an embodiment, the controller 112 on the flexible compression garment 502c can be configured to direct the medicament dispenser 110 on both of the flexible compression garments 502c and 502c' responsive to the sensed data from the one or more sensors 108 in the flexible compression garment 502c. The one or more medicament dispensers 110 can be similar or identical to any medicament dispenser disclosed herein. The one or more medicament dispensers 110 can include the same or different medicaments therein.

The one or more sensors 108 can be disposed on one or more regions of the flexible compression garment 502c or 502c' configured to detect a specific physiological characteristic or data related thereto, or from a body part therein or adjacent thereto. The body part can be any body part disclosed herein. For example, one or more sensors 108 can be disposed on the flexible compression garment 502c (e.g., near the knee) to detect data related a movement, load on a body part, or chemical composition of body fluid(s) adjacent thereto.

In an embodiment, at least one of the one or more sensors; one or more actuators; controller including any of the power source, control electrical circuitry, or interface, can include a waterproof construction or configuration, such as within the at least one flexible compression garment or at least one wearable device. For example, sweat produced during exercise can decrease or terminate proper functioning of electrical components, such as the controller, one or more sensors, or one or more actuators. In an embodiment, the controller or one or more actuators can be positioned in a waterproof or watertight material, such as a plastic, to ensure water (e.g., sweat) does not interfere with the proper functioning of the system. The waterproof construction can include discrete waterproof portions (e.g., pockets or compartments) in the at least one flexible compression garment or the at least one wearable device. Such waterproof portions can be reusable or resealable.

Figure 6:
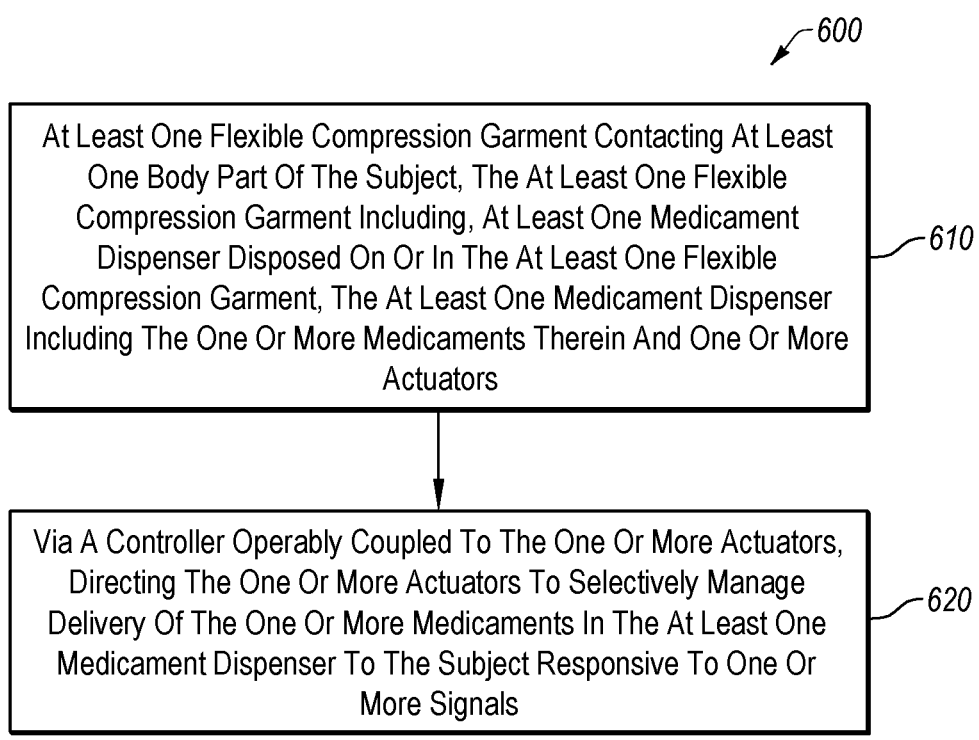
FIG. 6 is a flow chart of a method of dispensing one or more medicaments to a subject, according to an embodiment.

FIG. 6 is a flow chart of an embodiment of a method 600 of dispensing one or more medicaments to a subject. The method 600 includes an act 610 of at least one flexible compression garment contacting at least one body part of a subject, and an act 620 of via a controller operably coupled to one or more actuators, directing the one or more actuators to selectively manage delivery of the one or more medicaments in the medicament dispenser to the subject responsive to a signal.

The act 610 of the at least one flexible compression garment contacting at least one body part of a subject can include using any of the flexible compression garments, sensors, medicament dispensers, controllers, wearable devices, medicaments, or systems including the same disclosed herein. For example, the at least one flexible compression garment can include one or more medicament dispensers disposed thereon or therein. The one or more medicament dispensers can include one or more the medicaments therein. The one or more medicament dispensers can include one or more actuators. The flexible compression garment can include a controller operably coupled to the one or more actuators, the controller configured to direct the one or more actuators to selectively manage (e.g., deliver or alter delivery) of the one or more medicaments. In an embodiment, the system can include one or more sensors operably coupled to the controller. The one or more sensors can include any of the sensors disclosed herein.

The method 600 can include sensing one or more characteristics of the subject wearing the at least one compression garment via the one or more sensors thereon or therein. The one or more characteristics can include one or more physiological characteristic such as one or more of nerve activity of a body part of the subject, one or more body fluids of the subject, one or more chemicals in a body fluid of the subject, temperature in a body part of the subject, heart rate of the subject, pulse in a body part of the subject, oxygenation of a body part of the subject, acoustic emission from at least one joint or muscle of the subject, or swelling in a body part of the subject. The one or more characteristics can include one or more of a change in motion of travel of the subject, a load applied to the one or more sensors by a body part of the subject, pressure applied to the one or more sensors by a body part of the subject, tension applied to the one or more sensors by a body part of the subject, torque applied to the one or more sensors by a body part of the subject, velocity of at least a body part of the subject, acceleration of at least a body part of the subject, gait of the subject, or pace at which the subject moves. Some such characteristics can be referred to as environmental characteristics or physiological characteristics as context dictates. The one or more characteristics can include one or more of a load on a body part of the subject, pressure on a body part of the subject, tension on a body part of the subject, location of the subject, distance that the subject has traveled, a time of day, duration of an activity of the subject, duration since the last medicament was dispensed, duration since an direction to dispense a medicament was sent, or temperature of an ambient environment of the subject. Such characteristics can be referred to as other characteristics.

In an embodiment, the one or more sensors can include one or more temperature sensors each configured to sense a temperature of one or more body parts of the subject or an ambient environment around the subject. In an embodiment, the one or more sensors can include one or more oxygenation sensors each configured to sense blood oxygenation level in one or more body parts of the subject.

In an embodiment, the one or more sensors can include one or more chemical sensors each configured to sense a chemical level in a body fluid at one or more body parts of the subject. For example, the one or more chemical sensors can be configured to detect one or more of lactic acid, lactates, urea, salt, chloride, iron, potassium, sodium, cortisol, glutamate, prostaglandin, bradykinin, serotonin, adenosine triphosphate, pyruvate, other chemicals, or relative concentrations thereof in one or more body fluids. In an embodiment, the one or more chemical sensors can be configured to detect one or more of iron, hemoglobin, or blood plasma in a body part of the subject to determine if the subject is bleeding. In such an embodiment, the one or more medicaments can include any medicament disclosed herein, such as one or more of a coagulant, an anti-coagulant, or an antiseptic.

The act 620 of via a controller operably coupled to one or more actuators, directing the one or more actuators to selectively manage delivery of the one or more medicaments in the medicament dispenser to the subject responsive to a signal can be responsive to sensing feedback from one or more sensors or responsive to a controller (e.g., processor therein) determining that delivery of a medicament is required. In an embodiment, directing the one or more actuators to selectively manage delivery of the one or more medicaments in the medicament dispenser to the subject responsive to a signal can be initiated by user input specifying a selected delivery condition (e.g., initiate, increase, maintain, decrease, or cease delivery), such as with a user interface (e.g., flipping a switch or pressing a button).

In an embodiment, directing the one or more actuators includes providing one or more signals to the one or more actuators responsive to sensing the one or more characteristics. The one or more signals can include instructions effective to cause the one or more actuators to initiate, increase, maintain, decrease, or cease dispensing an amount of the one or more medicaments. The one or more signals can be provided from one or more of the controller, processor in the controller, or interface. In an embodiment, the interface is operably coupled to a remote device as disclosed above. The remote device can include any remote device herein. The remote device can include a user input device such as a user interface, which can be configured as any user input device or user interface herein. In an embodiment, directing the one or more actuators includes providing the signal to initiate a treatment regimen encoded in programming, such as a pre-programmed routine or regimen or a user programmed routine or regimen. Programs including instructions for any of the methods disclosed herein can be stored in the memory of the controller and can be accessed and operated by the processor.

In an embodiment, the one or more actuators can include a plurality of actuators each of which extends about at least a portion of the at least one flexible compression garment. In such an embodiment, directing one or more of the actuators can include directing or causing each of the plurality of actuators to manage deliver of one or more medicaments. In an embodiment, the at least one flexible compression garment includes a plurality of reservoirs. Each of the plurality of actuators can be operably coupled to at least a respective one (e.g., one, two, three, or all) of the plurality of reservoirs. In such an embodiment, directing the plurality of actuators can include selectively directing one or more of the plurality of actuators to selectively deliver the one or more medicaments from a selected one of the plurality of reservoirs, such as through one or more output apertures in the medicament dispenser. For example, responsive to a determination that a specific threshold level associated with physical condition corresponding a specific medicament, the controller can direct the actuator (e.g., only the actuator) associated with the specific medicament to manage delivery thereof. Such directing can include opening a valve or activating a pump. In such an embodiment, each of the plurality of reservoirs can include a different medicament therein.

In an embodiment, the one or more actuators can include one or more electroactive polymer actuators which can further include one or more actuator elements at least partially formed from ferroelectric polymers, dielectric elastomers, or electrostrictive graft elastomers. In such an embodiment, directing the one or more actuators can include providing or directing an electric current to the one or more electroactive polymer actuators.

In an embodiment, the one or more actuators can include one or more electroactive metallic actuators including one or more actuator elements at least partially formed from a shape memory material (e.g., a nickel-titanium shape memory alloy). In such an embodiment, directing the one or more actuators can include providing or directing an electric current to the shape memory material.

In an embodiment, the one or more actuators can include one or more motors including one or more micro-electro-mechanical motors. In such an embodiment, directing the one or more actuators includes providing or directing an electric current to the one or more micro-electro-mechanical motors.

In an embodiment, the one or more actuators can include a gear system and directing the one or more actuators can include providing or directing an electric current to the gear system.

In an embodiment, the one or more actuators can include a compressed gas system configured to provide inflow of compressed gas into or outflow of the compressed gas from at least a portion of the at least one flexible compression garment. In such an embodiment, directing the one or more actuators can include providing or directing an inflow of compressed gas into or outflow of the compressed gas from the at least a portion of the at least one flexible compression garment. The inflow of gas can be provided from a catalytic reaction product or a compressed gas reservoir. The catalytic reaction product can be a gas formed upon providing a catalyst to a reaction system responsive to the signal. The inflow of gas can be gas provided from a compressed gas reservoir via opening a valve responsive to the signal.

In an embodiment, the one or more actuators can include a constriction actuator positioned and configured to increase or decrease an interior space of at least a portion of the flexible compression. In such an embodiment, directing the one or more actuators can include causing or directing the one or more actuators to increase or decrease the interior space of the of the flexible compression garment.

In an embodiment, the medicament dispenser can include at least one protrusion (e.g., needle, or plurality of micro-protrusions) configured to at least partially penetrate the skin of the subject. In such an embodiment, directing the one or more actuators includes causing the at least one protrusion to at least partially penetrate at least a portion of skin (e.g., dermal tissue) of the subject and causing the one or more medicaments to dispense into the subject via the at least one needle. For example, the processor can direct the actuator to cause the needle to be inserted into the dermis of the subject. In an embodiment, the at least one protrusion can include a plurality of micro-protrusions configured to penetrate through at least a portion of the skin and transdermally deliver the one or more medicaments to the subject. In such an embodiment, directing the one or more actuators can include directing or causing the plurality of micro-protrusions to at least partially penetrate the skin (e.g., dermal tissue) of the subject and cause the one or more medicaments to be delivered to the subject. The one or more protrusions can include the one or more medicaments thereon (e.g., incorporated onto a surface thereof) or be configured to deliver the one or more medicaments therethrough (e.g., a hollow needle fluidly connected to a medicament reservoir). In such an embodiment, directing the at least one protrusion to at least partially penetrate the skin of the subject can include directing any of the actuators disclosed herein.

The controller can be configured to direct or cause the one or more actuators to manage delivery of the medicament by introducing the one or more protrusions into a soft tissue of a subject, such as into the dermal tissue. In such an embodiment, directing the one or more actuators can include directing the one or more actuators to cause the one or more protrusions to penetrate at least a portion of a soft tissue of a subject. In such an embodiment, actuating the one or more actuators can include directing the one or more actuators to cause the medicament to move from a reservoir, through a conduit (e.g., tube), through the one or more protrusions, and into the subject. Such directing can include opening a valve or activating a pump.

In an embodiment, the medicament dispenser can include one or more electrodes disposed in a region of the at least one flexible compression garment. The one or more electrodes can be configured to transdermally deliver the one or more medicaments to the subject adjacent to the region. The one or more electrodes can be used in conjunction with or apart from the one or more protrusions. In such an embodiment, directing the one or more actuators to selectively manage delivery of the one or more medicaments in the medicament dispenser can include providing an delivering an electrical current to the skin (e.g., dermal tissue) of the subject via the one or more electrodes.

In an embodiment, the one or more medicaments can be delivered to the skin (e.g., dermal tissue) of the subject via a material (e.g., a patch) having the one or more medicaments thereon, the material being disposed in the at least one flexible compression garment at least proximate to the one or more electrodes. In an embodiment, the one or more electrodes can including a medicament containing patch.

The method 600 can include wearing at least one flexible compression garment of a system on at least one body part of a subject. The method 600 can include wearing a second at least one flexible compression garment on another body part of the subject. The method 600 can include wearing one or more wearable devices on a body part of the subject, such a body part not disposed in the flexible compression garment.

The method 600 further can further include, with the one or more sensors, sensing the at least one physiological, environmental, or other characteristics associated with the subject or body part thereof. In an embodiment, sensing at least one physiological, environmental, or other characteristic associated with the subject includes sensing the at least one characteristic over a period of time. In an embodiment, the method further includes sending or communicating sensed data signals from the sensors to the controller, such as to the processor or interface. In an embodiment, directing the one or more actuators can include providing one or more signals to direct the one or more actuators to selectively initiate, selectively cease, selectively maintain, selectively increase, or selectively decrease delivery of the one or more medicaments after one or more time thresholds have elapsed as determined by a signal from a timer. In an embodiment, directing the one or more actuators is responsive to the at least one characteristic sensed by one or more sensors being over or below a threshold level. The at least one characteristic and associated threshold level can be any described herein, such as those characteristics indicative of the at least one subject or muscle being injured, exerting, or strained past a threshold.

As previously discussed, the at least one physiological, environmental, or other characteristics associated with the subject or body part thereof can include at least one of the a physical characteristic, a chemical characteristic (e.g., biochemical or biological), a physiological characteristic of the subject, change in motion of travel of a subject, change in direction of travel of a subject, load on a body part of a subject (e.g., load applied to the one or more sensors 108 by or through a body part of the subject 106), pressure on a body part of the subject (e.g., pressure applied to the one or more sensors 108 by or through a body part of the subject 106), tension on a body part of a subject (e.g., tension applied to the one or more sensors 108 by or through a body part of the subject 106), velocity of a body part of a subject, velocity of the subject, acceleration of a body part of the subject, temperature of a body part of the subject, pulse in a body part of the subject, location of the subject, elevation of the subject, duration of the motion or activity of the subject, gait of the subject, pace at which the subject moves, nerve activity of a subject, chemical excretion of a subject, temperature of the subject, temperature of the ambient environment of the subject, oxygenation of the subject, acoustic emission subject or variations, patterns or trends of any of the foregoing, or any other characteristic described herein.

In an embodiment, actuating the one or more actuators includes providing or applying voltage or current from the power source to the one or more actuators to cause actuation thereof. In an embodiment, actuating the one or more actuators can be carried out substantially in cycle, concert, sequence, or rhythm with the at least one characteristic sensed by the one or more sensors (e.g., actuating in rhythm with a pulse in a body part, heartbeat, or gait of the subject) or changes therein (e.g., increases or decreases in the sensed at least one characteristic).

In an embodiment, actuating the one or more actuators occurs according to an operational program, and can be initiated responsive to a sensed at least one characteristic. In an embodiment, the operational program is a pre-programmed operational program. In an embodiment, the at least one operational program can be related to (e.g., associated with, selected upon detection of, or correlated with) at least one sensed characteristic. For example, the at least one operation program can be configured to cause the medicament dispensers to release a vasodilator responsive to a pulse measurement being above a threshold value. In an embodiment, actuating the one or more actuators includes automatically selecting, via the controller (e.g., processor), the at least one operational program responsive the at least one sensed characteristic. In an embodiment, the method 600 can also include an act of programming (e.g., uploading, selecting, writing, or designating) the at least one operational program into the controller, such as via the interface. In an embodiment, the method can further include associating or correlating, with the processor, sensed data including one or more of the at least one sensed characteristic with at least one medicament.

In an embodiment, the method 600 can include indicating or displaying any of the information related to the system (e.g., status of medicament delivery, sensed data, threshold conditions, health condition of the subject, power status of the system, etc.) on the reporting device.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In an embodiment, the system is integrated in such a manner that the system operates as a unique system configured specifically for function of the medicament delivery device/system, and any associated computing devices of the system operate as specific use computers for purposes of the claimed system, and not general use computers. In an embodiment, at least one associated computing device of the system operates as specific use computers for purposes of the claimed system, and not general use computers. In an embodiment, at least one of the associated computing devices of the system are hardwired with a specific ROM to instruct the at least one computing device. In an embodiment, one of skill in the art recognizes that the medicament dispensing devices, systems, and methods effects an improvement at least in the technological field of at least one of health care or exercise science.

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A system for dispensing one or more medicaments to a subject, the system comprising:
   at least one flexible compression garment configured to be worn by the subject;
   at least one medicament dispenser disposed on or in the at least one flexible compression garment, the at least one medicament dispenser including the one or more medicaments therein and one or more actuators configured to selectively deliver the one or more medicaments the subject when the at least one flexible compression garment is worn by the subject;
   a controller operably coupled to the one or more actuators, the controller configured to direct the one or more actuators to manage delivery of the one or more medicaments from the at least one medicament dispenser; and
   one or more sensors operably coupled to the controller, the one or more sensors being configured to sense physiological data of the subject, wherein the one or more sensors include one or more of an accelerometer, a pedometer, a tension sensor, a pressure sensor, an electromyographical sensor, a mechanomyographic sensor, a kinematic sensor, a kinetic sensor, a pulse sensor, a chemical sensor, an oximeter, an optical sensor, an acoustic sensor, or a temperature sensor;
   wherein the controller is configured to direct the one or more actuators to selectively deliver the one or more medicaments to the subject responsive to the sensed physiological data of the subject.

2. The system of claim 1, wherein the one or more sensors are located in the at least one flexible compression garment.

3. The system of claim 1, wherein at least one of the one or more sensors is separately located from the at least one flexible compression garment.

4. The system of claim 1, wherein the one or more sensors are configured to detect one or more of nerve activity of a body part of the subject, one or more body fluids of the subject, one or more chemicals in a body fluid of the subject, temperature in a body part of the subject, heart rate of the subject, pulse in a body part of the subject, oxygenation of a body part of the subject, acoustic emission from at least one joint or muscle of the subject, or swelling in a body part of the subject.

5. The system of claim 1, wherein the one or more sensors are configured to detect one or more of a change in motion of travel of the subject, a load applied to the one or more sensors by a body part of the subject, pressure applied to the one or more sensors by a body part of the subject, tension applied to the one or more sensors by a body part of the subject, torque applied to the one or more sensors by a body part of the subject, velocity of at least a body part of the subject, acceleration of at least a body part of the subject, location of the subject, gait of the subject, or pace at which the subject moves.

6. The system of claim 1, wherein the one or more sensors are configured to detect one or more of a load on a body part of the subject, pressure on a body part of the subject, tension on a body part of the subject, location of the subject, distance that the subject has traveled, or temperature of the subject.

7. The system of claim 1, wherein the one or more sensors are operably coupled to the controller via a wireless connection.

8. The system of claim 1, wherein the at least one flexible compression garment is formed at least partially from at least one of neoprene, nylon, synthetic rubber, or fabric.

9. The system of claim 1, wherein the at least one flexible compression garment is substantially tubular and configured to generally conform to at least one body part of the subject.

10. The system of claim 9, wherein the at least one body part includes at least a portion of an arm, at least a portion of an elbow, at least a portion of a forearm, at least a portion of a wrist, at least a portion of a hand, at least a portion of a thigh, at least a portion of a knee, at least a portion of a lower leg, at least a portion of an ankle, at least a portion of a foot, at least a portion of a neck, at least a portion of an abdomen, at least a portion of a back, at least a portion of a hip, at least a portion of a gluteus maximus, at least a portion of a waist, or at least a portion of a chest.

11. The system of claim 9, wherein the at least one flexible compression garment includes an article of clothing.

12. The system of claim 1, wherein the one or more actuators include at least one of one or more electroactive polymer actuators, one or more electroactive metallic actuators, one or more thermally active polymer actuators, one or more motors, one or more hydraulic actuators, one or more plungers, one or more pneumatic actuators, or one or more piezoelectric actuators.

13. The system of claim 12, wherein the one or more motors include one or more micro-electro-mechanical motors.

14. The system of claim 1, wherein the one or more actuators include a gear system.

15. The system of claim 1, wherein the one or more actuators include a constriction actuator positioned and configured to at least one of increase or decrease an interior space of at least a portion of the flexible compression garment.

16. The system of claim 1, wherein the one or more actuators include at least one fluid displacement actuator.

17. The system of claim 16, wherein the at least one fluid displacement actuator includes one or more piezoelectric actuators, one or more springs, one or more solenoids, one or more magnets, one or more motors, one or more micro-motors, or one or more compressed gas actuators.

18. The system of claim 1, further including a power source operably coupled to at least one of the one or more actuators or the controller.

19. The system of claim 1, wherein the at least one medicament dispenser is configured to provide one or more of a topical, a transdermal, or an intramuscular delivery of the one or more medicaments to soft tissue of the subject.

20. The system of claim 1, wherein the at least one medicament dispenser includes one or more of a plurality of pores, one or more needles, one or more micro-protrusions, one or more micro-jets, one or more electrodes, one or more energy source, an iontophoretic device, one or more medicament patches, or one or more tubes.

21. The system of claim 1, wherein,
the at least one medicament dispenser includes at least one reservoir, one or more output apertures, and one or more conduits therebetween; and
the controller is configured to direct the one or more actuators to manage delivery of the one or more medicaments from the at least one reservoir and through the one or more output apertures.

22. The system of claim 1, wherein the one or more output apertures are disposed in a region of the at least one flexible compression garment.

23. The system of claim 1, wherein the at least one medicament dispenser includes a plurality of micro-protrusions disposed in a region of the at least one flexible garment, the plurality of micro-protrusions configured to transdermally deliver the one or more medicament to a region of the subject adjacent thereto.

24. The system of claim 23, wherein,
the one or more micro-protrusions incorporate the one or more medicaments; and
the controller is configured to direct the one or more actuators to manage delivery of the one or more medicaments by introducing the one or more micro-protrusions into dermal tissue of the subject.

25. The system of claim 1, wherein the at least one medicament dispenser includes a plurality of electrodes disposed in a region of the at least one flexible garment, the plurality of electrodes configured to transdermally deliver the one or more medicaments to a region of the subject adjacent thereto.

26. The system of claim 1, wherein the at least one medicament dispenser includes a plurality of output apertures each of which includes a plurality of pores disposed in a region of the at least one flexible garment configured to deliver the one or more medicament to a region of the subject adjacent thereto, each of the plurality of pores being operably coupled to a medicament reservoir via a conduit therebetween.

27. The system of claim 1, wherein,
the at least one medicament dispenser includes a single needle configured to deliver the one or more medicaments; and
the one or more actuators are configured to insert the single needle into the subject and to pump one or more medicaments into the subject via the single needle.

28. The system of claim 1, wherein the one or more medicaments includes one or more of an anesthetic, an analgesic, an anti-inflammatory, rubefacient, a warming agent, a coagulant, an anti-coagulant, a cooling agent, a salicylate, a vasodilator, a vasoconstrictor, an antiseptic, a hormone, a steroid, a corticosteroid, a vitamin, a nutrient, or a mineral.

29. The system of claim 1,
wherein the controller is configured to receive one or more signals from one or more sensors operably coupled to the controller and direct the one or more actuators responsive to the one or more signals.

30. The system of claim 29, wherein,
the one or more sensors are configured to sense at least one physical characteristic including one or more of decreased muscle oxygenation, decreased blood flow, increased localized pressure, displacement of one or more sensors, depletion of chemical components in a body fluid, increase of lactic acid in a body fluid, altered echogenicity, or electrical signals indicative of the strength of muscle contractions of the subject and communicate the at least one physical characteristic to the controller;
the controller is configured to determine if a body part of the subject is fatigued, swollen, or strained based on the at least one physical characteristic; and
responsive to the determination by the controller, the controller is configured to direct the one or more actuators to deliver the one or more medicaments.

31. The system of claim 29, wherein,
the one or more sensors are configured to sense at least one physical characteristic including one or more of decreased muscle oxygenation, decreased blood flow, increased localized pressure, displacement of one or more sensors, depletion of a chemical component in a body fluid, increase of lactic acid in a body fluid, altered echogenicity, or electrical signals indicative of the strength of muscle contractions of the subject and communicate the at least one physical characteristic to the controller;
the controller includes a processor configured to determine if a body part of the subject is fatigued, swollen, or strained based on a threshold level of the at least one physical characteristic; and
responsive to the determination by the processor, the controller is configured to direct the one or more actuators to selectively initiate, increase, maintain, decrease, or terminate delivery of the one or more medicaments.

32. The system of claim 1, further including an interface operably connected to the controller.

33. The system of claim 32, wherein the interface is operably coupled to at least one remote device.

34. The system of claim 33, wherein the remote device includes a communication device, a cellular phone, a desktop computer, a tablet computer, a laptop computer, or an external switch.

35. The system of claim 32, wherein the interface includes a user input device and the controller is configured to receive user input.

36. The system of claim 35, wherein the user input includes one or more of programming instructions or control instructions.

37. The system of claim 32, wherein the interface includes at least one reporting device.

38. They system of claim 37, wherein the at least one reporting device is configured to indicate to a user one or more of that the one or more medicaments have or have not been delivered, that the system has sensed a need to deliver the one or more medicaments, or a report with information from at least one of the one or more sensors.

39. The system of claim 1, wherein the controller is configured to generate a report with information from one or more sensors or the controller.

40. The system of claim 1, wherein the controller includes a processor having programming to direct the one or more actuators to initiate delivery, maintain delivery, or cease delivery of the one or more medicaments from the at least one medicament dispenser.

41. The system of claim 40, wherein the processor is programmable via an interface operably connected to the controller.

42. A method of dispensing one or more medicaments to a subject, the method comprising:
 at least one flexible compression garment contacting at least one body part of the subject, the at least one flexible compression garment including,
  at least one medicament dispenser disposed on or in the at least one flexible compression garment, the at least one medicament dispenser including the one or more medicaments therein and one or more actuators; and
 via one or more sensors, detecting one or more of physiological data associated with the subject, the one or more sensors including at least one of an accelerometer, a pedometer, a tension sensor, a pressure sensor, an electromyographical sensor, a mechanomyographic sensor, a kinematic sensor, a kinetic sensor, a pulse sensor, a chemical sensor, an oximeter, an optical sensor, an acoustic sensor, or a temperature sensor;
 communicating sensed physiological data to a controller operably coupled to the one or more actuators and the one or more sensors; and
 via the controller operably coupled to the one or more actuators, directing the one or more actuators to selectively manage delivery of the one or more medicaments in the at least one medicament dispenser to the subject responsive to one or more signals from the controller in response to the sensed physiological data.

43. A system for dispensing one or more medicaments to a subject, the system comprising:
 at least one flexible compression garment;
 at least one sensor disposed in or on the at least one flexible compression garment, the at least one sensor being configured to sense physiological data, wherein the at least one sensor includes one or more of an accelerometer, a pedometer, a tension sensor, a pressure sensor, an electromyographical sensor, a mechanomyographic sensor, a kinematic sensor, a kinetic sensor, a pulse sensor, an oximeter, an optical sensor, an acoustic sensor, or a temperature sensor;
 at least one medicament dispenser disposed on or in the at least one flexible compression garment, the at least one medicament dispenser including,
  the one or more medicaments therein; and
  one or more actuators configured to selectively deliver the one or more medicaments; and
 a controller operably coupled to the at least one sensor and the one or more actuators, the controller configured to receive sensed physiological data from the at least one sensor, determine whether the sensed physiological data indicates a need for dispensing the one or more medicaments, and direct the one or more actuators to manage delivery of the one or more medicaments from the at least one medicament dispenser, responsive to the determination.

44. The system of claim 1 wherein:
 the controller is configured to receive one or more signals from one or more sensors operably coupled to the controller and direct the one or more actuators responsive to the one or more signals;
 the one or more sensors include a myography sensor configured to sense electrical signals and communicate the sensed electrical signals to the controller;
 the controller is configured to determine if a body part of the subject is fatigued, swollen, or strained based on the sensed electrical signals; and
 responsive to the determination by the controller, the controller is configured to direct the one or more actuators to deliver the one or more medicaments.

45. The system of claim 1 wherein:
 the controller is configured to receive one or more signals from one or more sensors operably coupled to the controller and direct the one or more actuators responsive to the one or more signals;
 the one or more sensors include near infrared sensor configured to sense light signals indicative of oxygenation in the subject and communicate the sensed light signals to the controller;
 the controller is configured to determine if a body part of the subject is fatigued, swollen, or strained based on the sensed light signals; and
 responsive to the determination by the controller, the controller is configured to direct the one or more actuators to deliver the one or more medicaments.

46. The system of claim 1 wherein the controller is configured to direct the one or more actuators to increase or decrease an amount of the one or more medicaments being delivered responsive to the sensed physiological data.

47. The system of claim 1 wherein the controller is configured to direct the one or more actuators to selectively deliver the one or more medicaments responsive to at least one characteristic of the sensed physiological data exceeding a predetermined threshold level.

48. The method of claim 42, wherein directing the one or more actuators to selectively manage delivery of the one or more medicaments in the at least one medicament dispenser to the subject responsive to one or more signals from the controller in response to the sensed physiological data includes directing the one or more actuators to increase or decrease an amount of the one or more medicaments being delivered responsive to the sensed physiological data.

49. The method of claim 42, wherein directing the one or more actuators to selectively manage delivery of the one or more medicaments in the at least one medicament dispenser to the subject responsive to one or more signals from the controller in response to the sensed physiological data includes directing the one or more actuators to selectively deliver the one or more medicaments responsive to at least one characteristic of the sensed physiological data exceeding a predetermined threshold level.

50. The system of claim 43 wherein the controller is configured to direct the one or more actuators to increase or decrease an amount of the one or more medicaments being delivered responsive to the sensed physiological data.

51. The system of claim 43 wherein the controller is configured to direct the one or more actuators to selectively deliver the one or more medicaments responsive to at least one characteristic of the sensed physiological data exceeding a predetermined threshold level.

* * * * *